United States Patent
Zhang et al.

(10) Patent No.: US 9,910,026 B2
(45) Date of Patent: Mar. 6, 2018

(54) HIGH TEMPERATURE TRACERS FOR DOWNHOLE DETECTION OF PRODUCED WATER

(71) Applicants: Zhihui Zhang, Katy, TX (US); Guijun Deng, The Woodlands, TX (US); Zhiyue Xu, Cypress, TX (US); Guobin Ma, Houston, TX (US); Ke Wang, Sugar Land, TX (US)

(72) Inventors: Zhihui Zhang, Katy, TX (US); Guijun Deng, The Woodlands, TX (US); Zhiyue Xu, Cypress, TX (US); Guobin Ma, Houston, TX (US); Ke Wang, Sugar Land, TX (US)

(73) Assignee: BAKER HUGHES, A GE COMPANY, LLC, Houston, TX (US)

(*) Notice: Subject to any disclaimer, the term of this patent is extended or adjusted under 35 U.S.C. 154(b) by 141 days.

(21) Appl. No.: 14/601,305

(22) Filed: Jan. 21, 2015

(65) Prior Publication Data
US 2016/0209391 A1    Jul. 21, 2016

(51) Int. Cl.
*G01N 33/28*    (2006.01)
*E21B 47/11*    (2012.01)
*E21B 47/10*    (2012.01)

(52) U.S. Cl.
CPC ..... *G01N 33/2847* (2013.01); *E21B 47/1015* (2013.01); *G01N 33/2882* (2013.01)

(58) Field of Classification Search
CPC .................................................. G01N 33/2847
See application file for complete search history.

(56) References Cited

U.S. PATENT DOCUMENTS

| | | | |
|---|---|---|---|
| 1,468,905 A | 9/1923 | Herman | |
| 2,189,697 A | 2/1940 | Baker | |
| 2,222,233 A | 11/1940 | Mize | |
| 2,225,143 A | 12/1940 | Baker et al. | |
| 2,238,895 A | 4/1941 | Gage | |
| 2,261,292 A | 11/1941 | Salnikov | |
| 2,294,648 A | 9/1942 | Ansel | |
| 2,301,624 A | 11/1942 | Holt | |
| 2,352,993 A * | 7/1944 | Albertson | G01V 5/08 250/260 |

(Continued)

FOREIGN PATENT DOCUMENTS

| | | |
|---|---|---|
| CA | 2783241 A1 | 6/2011 |
| CA | 2783346 A1 | 6/2011 |

(Continued)

OTHER PUBLICATIONS

Reid, Literature Evaluation of Induced Groundwater Tracers, Field Tracer Techniques, and Hydrodynamic Dispersion Values in Porous Media, Aug. 1981, Texas Tech University Thesis, pp. i-1, 22-28, 35, 42-44, 55, 62, & 69.*

(Continued)

*Primary Examiner* — David Porta
*Assistant Examiner* — Jeremy S Valentiner
(74) *Attorney, Agent, or Firm* — Cantor Colburn LLP

(57) ABSTRACT

A tracer composite comprises a tracer disposed in a metal-based carrier which comprises: a cellular nanomatrix and a metal matrix disposed in the cellular nanomatrix, wherein the tracer is detectable at a range of from about 1 ppt to about 1,000 ppm.

21 Claims, 4 Drawing Sheets

(56) References Cited

U.S. PATENT DOCUMENTS

| | | |
|---|---|---|
| 2,394,843 A | 2/1946 | Cooke et al. |
| 2,672,199 A | 3/1954 | McKenna |
| 2,753,941 A | 7/1956 | Hebard et al. |
| 2,754,910 A | 7/1956 | Derrick et al. |
| 2,933,136 A | 4/1960 | Ayers et al. |
| 2,983,634 A | 5/1961 | Budininkas et al. |
| 3,057,405 A | 10/1962 | Mallinger |
| 3,066,391 A | 12/1962 | Vordahl |
| 3,106,959 A | 10/1963 | Huitt et al. |
| 3,142,338 A | 7/1964 | Brown |
| 3,152,009 A | 10/1964 | Delong |
| 3,196,949 A | 7/1965 | Thomas |
| 3,242,988 A | 3/1966 | McGuire et al. |
| 3,316,748 A | 5/1967 | Lang et al. |
| 3,326,291 A | 6/1967 | Zandmer et al. |
| 3,343,537 A | 9/1967 | Graham |
| 3,347,317 A | 10/1967 | Zandmer |
| 3,347,714 A | 10/1967 | Broverman et al. |
| 3,390,724 A | 7/1968 | Caldwell |
| 3,395,758 A | 8/1968 | Kelly et al. |
| 3,406,101 A | 10/1968 | Kilpatrick |
| 3,416,918 A | 12/1968 | Henry |
| 3,465,181 A | 9/1969 | Colby et al. |
| 3,513,230 A | 5/1970 | Rhees et al. |
| 3,602,305 A | 8/1971 | Kisling |
| 3,637,446 A | 1/1972 | Elliott et al. |
| 3,645,331 A | 2/1972 | Maurer et al. |
| 3,660,049 A | 5/1972 | Benjamin |
| 3,765,484 A | 10/1973 | Hamby, Jr. et al. |
| 3,768,563 A | 10/1973 | Blount |
| 3,775,823 A | 12/1973 | Adolph et al. |
| 3,878,889 A | 4/1975 | Seabourn |
| 3,894,850 A | 7/1975 | Kovalchuk et al. |
| 3,924,677 A | 12/1975 | Prenner et al. |
| 4,010,583 A | 3/1977 | Highberg |
| 4,039,717 A | 8/1977 | Titus |
| 4,050,529 A | 9/1977 | Tagirov et al. |
| 4,157,732 A | 6/1979 | Fonner |
| 4,248,307 A | 2/1981 | Silberman et al. |
| 4,284,137 A | 8/1981 | Taylor |
| 4,292,377 A | 9/1981 | Petersen et al. |
| 4,372,384 A | 2/1983 | Kinney |
| 4,373,584 A | 2/1983 | Silberman et al. |
| 4,373,952 A | 2/1983 | Parent |
| 4,374,543 A | 2/1983 | Richardson |
| 4,384,616 A | 5/1983 | Dellinger |
| 4,395,440 A | 7/1983 | Abe et al. |
| 4,399,871 A | 8/1983 | Adkins et al. |
| 4,407,368 A | 10/1983 | Erbstoesser |
| 4,422,508 A | 12/1983 | Rutledge, Jr. et al. |
| 4,452,311 A | 6/1984 | Speegle et al. |
| 4,475,729 A | 10/1984 | Costigan |
| 4,498,543 A | 2/1985 | Pye et al. |
| 4,499,048 A | 2/1985 | Hanejko |
| 4,499,049 A | 2/1985 | Hanejko |
| 4,524,825 A | 6/1985 | Fore |
| 4,526,840 A | 7/1985 | Jerabek |
| 4,534,414 A | 8/1985 | Pringle |
| 4,539,175 A | 9/1985 | Lichti et al. |
| 4,554,986 A | 11/1985 | Jones |
| 4,640,354 A | 2/1987 | Boisson |
| 4,664,962 A | 5/1987 | Desmarais, Jr. |
| 4,668,470 A | 5/1987 | Gilman et al. |
| 4,673,549 A | 6/1987 | Ecer |
| 4,674,572 A | 6/1987 | Gallus |
| 4,678,037 A | 7/1987 | Smith |
| 4,681,133 A | 7/1987 | Weston |
| 4,688,641 A | 8/1987 | Knieriemen |
| 4,693,863 A | 9/1987 | Del Corso et al. |
| 4,703,807 A | 11/1987 | Weston |
| 4,706,753 A | 11/1987 | Ohkochi et al. |
| 4,708,202 A | 11/1987 | Sukup et al. |
| 4,708,208 A | 11/1987 | Halbardier |
| 4,709,761 A | 12/1987 | Setterberg, Jr. |
| 4,714,116 A | 12/1987 | Brunner |
| 4,716,964 A | 1/1988 | Erbstoesser et al. |
| 4,719,971 A | 1/1988 | Owens |
| 4,721,159 A | 1/1988 | Ohkochi et al. |
| 4,738,599 A | 4/1988 | Shilling |
| 4,741,973 A | 5/1988 | Condit et al. |
| 4,768,588 A | 9/1988 | Kupsa |
| 4,775,598 A | 10/1988 | Jaeckel |
| 4,784,226 A | 11/1988 | Wyatt |
| 4,805,699 A | 2/1989 | Halbardier |
| 4,817,725 A | 4/1989 | Jenkins |
| 4,834,184 A | 5/1989 | Streich et al. |
| H0635 H | 6/1989 | Johnson et al. |
| 4,850,432 A | 7/1989 | Porter et al. |
| 4,853,056 A | 8/1989 | Hoffman |
| 4,869,324 A | 9/1989 | Holder |
| 4,869,325 A | 9/1989 | Halbardier |
| 4,880,059 A | 11/1989 | Brandell et al. |
| 4,889,187 A | 12/1989 | Terrell et al. |
| 4,890,675 A | 1/1990 | Dew |
| 4,901,794 A | 2/1990 | Baugh et al. |
| 4,909,320 A | 3/1990 | Hebert et al. |
| 4,929,415 A | 5/1990 | Okazaki |
| 4,932,474 A | 6/1990 | Schroeder, Jr. et al. |
| 4,938,309 A | 7/1990 | Emdy |
| 4,938,809 A | 7/1990 | Das et al. |
| 4,944,351 A | 7/1990 | Eriksen et al. |
| 4,949,788 A | 8/1990 | Szarka et al. |
| 4,952,902 A | 8/1990 | Kawaguchi et al. |
| 4,975,412 A | 12/1990 | Okazaki et al. |
| 4,977,958 A | 12/1990 | Miller |
| 4,981,177 A | 1/1991 | Carmody et al. |
| 4,986,361 A | 1/1991 | Mueller et al. |
| 4,997,622 A | 3/1991 | Regazzoni et al. |
| 5,006,044 A | 4/1991 | Walker, Sr. et al. |
| 5,010,955 A | 4/1991 | Springer |
| 5,036,921 A | 8/1991 | Pittard et al. |
| 5,048,611 A | 9/1991 | Cochran |
| 5,049,165 A | 9/1991 | Tselesin |
| 5,061,323 A | 10/1991 | Deluccia |
| 5,063,775 A | 11/1991 | Walker, Sr. et al. |
| 5,073,207 A | 12/1991 | Faure et al. |
| 5,074,361 A | 12/1991 | Brisco et al. |
| 5,076,869 A | 12/1991 | Bourell et al. |
| 5,084,088 A | 1/1992 | Okazaki |
| 5,087,304 A | 2/1992 | Chang et al. |
| 5,090,480 A | 2/1992 | Pittard et al. |
| 5,095,988 A | 3/1992 | Bode |
| 5,103,911 A | 4/1992 | Heijnen |
| 5,117,915 A | 6/1992 | Mueller et al. |
| 5,161,614 A | 11/1992 | Wu et al. |
| 5,171,734 A | 12/1992 | Sanjurjo et al. |
| 5,178,216 A | 1/1993 | Giroux et al. |
| 5,181,571 A | 1/1993 | Mueller et al. |
| 5,183,631 A | 2/1993 | Kugimiya et al. |
| 5,188,182 A | 2/1993 | Echols, III et al. |
| 5,188,183 A | 2/1993 | Hopmann et al. |
| 5,204,055 A | 4/1993 | Sachs et al. |
| 5,222,867 A | 6/1993 | Walker, Sr. et al. |
| 5,226,483 A | 7/1993 | Williamson, Jr. |
| 5,228,518 A | 7/1993 | Wilson et al. |
| 5,234,055 A | 8/1993 | Cornette |
| 5,252,365 A | 10/1993 | White |
| 5,253,714 A | 10/1993 | Davis et al. |
| 5,271,468 A | 12/1993 | Streich et al. |
| 5,282,509 A | 2/1994 | Schurr |
| 5,292,478 A | 3/1994 | Scorey |
| 5,293,940 A | 3/1994 | Hromas et al. |
| 5,304,260 A | 4/1994 | Aikawa et al. |
| 5,304,588 A | 4/1994 | Boysen et al. |
| 5,309,874 A | 5/1994 | Willermet et al. |
| 5,310,000 A | 5/1994 | Arterbury et al. |
| 5,316,598 A | 5/1994 | Chang et al. |
| 5,318,746 A | 6/1994 | Lashmore |
| 5,352,522 A | 10/1994 | Kugimiya et al. |
| 5,380,473 A | 1/1995 | Bogue et al. |
| 5,387,380 A | 2/1995 | Cima et al. |
| 5,392,860 A | 2/1995 | Ross |
| 5,394,236 A * | 2/1995 | Murnick ............... G01N 21/62 356/308 |

(56) References Cited

U.S. PATENT DOCUMENTS

| | | |
|---|---|---|
| 5,394,941 A | 3/1995 | Venditto et al. |
| 5,398,754 A | 3/1995 | Dinhoble |
| 5,407,011 A | 4/1995 | Layton |
| 5,409,555 A | 4/1995 | Fujita et al. |
| 5,411,082 A | 5/1995 | Kennedy |
| 5,417,285 A | 5/1995 | Van Buskirk et al. |
| 5,425,424 A | 6/1995 | Reinhardt et al. |
| 5,427,177 A | 6/1995 | Jordan, Jr. et al. |
| 5,435,392 A | 7/1995 | Kennedy |
| 5,439,051 A | 8/1995 | Kennedy et al. |
| 5,454,430 A | 10/1995 | Kennedy et al. |
| 5,456,317 A | 10/1995 | Hood et al. |
| 5,456,327 A | 10/1995 | Denton et al. |
| 5,464,062 A | 11/1995 | Blizzard, Jr. |
| 5,472,048 A | 12/1995 | Kennedy et al. |
| 5,474,131 A | 12/1995 | Jordan, Jr. et al. |
| 5,477,923 A | 12/1995 | Jordan, Jr. et al. |
| 5,479,986 A | 1/1996 | Gano et al. |
| 5,506,055 A | 4/1996 | Dorfman et al. |
| 5,507,439 A | 4/1996 | Story |
| 5,511,620 A | 4/1996 | Baugh et al. |
| 5,524,699 A | 6/1996 | Cook |
| 5,526,880 A | 6/1996 | Jordan, Jr. et al. |
| 5,526,881 A | 6/1996 | Martin et al. |
| 5,529,746 A | 6/1996 | Knoss et al. |
| 5,533,573 A | 7/1996 | Jordan, Jr. et al. |
| 5,536,485 A | 7/1996 | Kume et al. |
| 5,558,153 A | 9/1996 | Holcombe et al. |
| 5,601,924 A | 2/1997 | Beane |
| 5,607,017 A | 3/1997 | Owens et al. |
| 5,623,993 A | 4/1997 | Van Buskirk et al. |
| 5,623,994 A | 4/1997 | Robinson |
| 5,636,691 A | 6/1997 | Hendrickson et al. |
| 5,641,023 A | 6/1997 | Ross et al. |
| 5,647,444 A | 7/1997 | Williams |
| 5,665,289 A | 9/1997 | Chung et al. |
| 5,677,372 A | 10/1997 | Yamamoto et al. |
| 5,685,372 A | 11/1997 | Gano |
| 5,701,576 A | 12/1997 | Fujita et al. |
| 5,707,214 A | 1/1998 | Schmidt |
| 5,709,269 A | 1/1998 | Head |
| 5,720,344 A | 2/1998 | Newman |
| 5,728,195 A | 3/1998 | Eastman et al. |
| 5,765,639 A | 6/1998 | Muth |
| 5,772,735 A | 6/1998 | Sehgal et al. |
| 5,782,305 A | 7/1998 | Hicks |
| 5,797,454 A | 8/1998 | Hipp |
| 5,826,652 A | 10/1998 | Tapp |
| 5,826,661 A | 10/1998 | Parker et al. |
| 5,829,520 A | 11/1998 | Johnson |
| 5,836,396 A | 11/1998 | Norman |
| 5,857,521 A | 1/1999 | Ross et al. |
| 5,881,816 A | 3/1999 | Wright |
| 5,896,819 A | 4/1999 | Turila et al. |
| 5,902,424 A | 5/1999 | Fujita et al. |
| 5,934,372 A | 8/1999 | Muth |
| 5,941,309 A | 8/1999 | Appleton |
| 5,960,881 A | 10/1999 | Allamon et al. |
| 5,985,466 A | 11/1999 | Atarashi et al. |
| 5,988,287 A | 11/1999 | Jordan, Jr. et al. |
| 5,990,051 A | 11/1999 | Ischy et al. |
| 5,992,452 A | 11/1999 | Nelson, II |
| 5,992,520 A | 11/1999 | Schultz et al. |
| 6,007,314 A | 12/1999 | Nelson, II |
| 6,024,915 A | 2/2000 | Kume et al. |
| 6,032,735 A | 3/2000 | Echols |
| 6,036,777 A | 3/2000 | Sachs |
| 6,047,773 A | 4/2000 | Zeltmann et al. |
| 6,050,340 A | 4/2000 | Scott |
| 6,069,313 A | 5/2000 | Kay |
| 6,076,600 A | 6/2000 | Vick, Jr. et al. |
| 6,079,496 A | 6/2000 | Hirth |
| 6,085,837 A | 7/2000 | Massinon et al. |
| 6,095,247 A | 8/2000 | Streich et al. |
| 6,119,783 A | 9/2000 | Parker et al. |
| 6,142,237 A | 11/2000 | Christmas et al. |
| 6,161,622 A | 12/2000 | Robb |
| 6,167,970 B1 | 1/2001 | Stout et al. |
| 6,170,583 B1 | 1/2001 | Boyce |
| 6,173,779 B1 | 1/2001 | Smith |
| 6,176,323 B1 | 1/2001 | Weirich et al. |
| 6,189,616 B1 | 2/2001 | Gano et al. |
| 6,189,618 B1 | 2/2001 | Beeman et al. |
| 6,213,202 B1 | 4/2001 | Read, Jr. |
| 6,220,350 B1 | 4/2001 | Brothers et al. |
| 6,220,357 B1 | 4/2001 | Carmichael et al. |
| 6,228,904 B1 | 5/2001 | Yadav et al. |
| 6,237,688 B1 | 5/2001 | Burleson et al. |
| 6,238,280 B1 | 5/2001 | Ritt et al. |
| 6,241,021 B1 | 6/2001 | Bowling |
| 6,248,399 B1 | 6/2001 | Hehmann |
| 6,250,392 B1 | 6/2001 | Muth |
| 6,261,432 B1 | 7/2001 | Huber et al. |
| 6,273,187 B1 | 8/2001 | Voisin, Jr. et al. |
| 6,276,452 B1 | 8/2001 | Davis et al. |
| 6,276,457 B1 | 8/2001 | Moffatt et al. |
| 6,279,656 B1 | 8/2001 | Sinclair et al. |
| 6,287,445 B1 | 9/2001 | Lashmore et al. |
| 6,302,205 B1 | 10/2001 | Ryll |
| 6,315,041 B1 | 11/2001 | Carlisle et al. |
| 6,315,050 B2 | 11/2001 | Vaynshteyn et al. |
| 6,325,148 B1 | 12/2001 | Trahan et al. |
| 6,328,110 B1 | 12/2001 | Joubert |
| 6,341,653 B1 | 1/2002 | Firmaniuk et al. |
| 6,341,747 B1 | 1/2002 | Schmidt et al. |
| 6,349,766 B1 | 2/2002 | Bussear et al. |
| 6,354,372 B1 | 3/2002 | Carisella et al. |
| 6,354,379 B2 | 3/2002 | Miszewski et al. |
| 6,357,322 B1 | 3/2002 | Dolan et al. |
| 6,357,332 B1 | 3/2002 | Vecchio |
| 6,371,206 B1 | 4/2002 | Mills |
| 6,372,346 B1 | 4/2002 | Toth |
| 6,382,244 B2 | 5/2002 | Vann |
| 6,390,195 B1 | 5/2002 | Nguyen et al. |
| 6,390,200 B1 | 5/2002 | Allamon et al. |
| 6,394,180 B1 | 5/2002 | Berscheidt et al. |
| 6,394,185 B1 | 5/2002 | Constien |
| 6,397,950 B1 | 6/2002 | Streich et al. |
| 6,401,547 B1 | 6/2002 | Hatfield et al. |
| 6,403,210 B1 | 6/2002 | Stuivinga et al. |
| 6,408,946 B1 | 6/2002 | Marshall et al. |
| 6,419,023 B1 | 7/2002 | George et al. |
| 6,439,313 B1 | 8/2002 | Thomeer et al. |
| 6,446,117 B1 | 9/2002 | Gebauer |
| 6,457,525 B1 | 10/2002 | Scott |
| 6,467,546 B2 | 10/2002 | Allamon et al. |
| 6,470,965 B1 | 10/2002 | Winzer |
| 6,491,097 B1 | 12/2002 | Oneal et al. |
| 6,491,116 B2 | 12/2002 | Berscheidt et al. |
| 6,513,598 B2 | 2/2003 | Moore et al. |
| 6,513,600 B2 | 2/2003 | Ross |
| 6,540,033 B1 | 4/2003 | Sullivan et al. |
| 6,543,543 B2 | 4/2003 | Muth |
| 6,561,275 B2 | 5/2003 | Glass et al. |
| 6,588,507 B2 | 7/2003 | Dusterhoft et al. |
| 6,591,915 B2 | 7/2003 | Burris et al. |
| 6,601,648 B2 | 8/2003 | Ebinger |
| 6,601,650 B2 | 8/2003 | Sundararajan |
| 6,609,569 B2 | 8/2003 | Howlett et al. |
| 6,612,826 B1 | 9/2003 | Bauer et al. |
| 6,613,383 B1 | 9/2003 | George et al. |
| 6,619,400 B2 | 9/2003 | Brunet |
| 6,634,428 B2 | 10/2003 | Krauss et al. |
| 6,662,886 B2 | 12/2003 | Russell |
| 6,675,889 B1 | 1/2004 | Mullins et al. |
| 6,699,305 B2 | 3/2004 | Myrick |
| 6,712,153 B2 | 3/2004 | Turley et al. |
| 6,712,797 B1 | 3/2004 | Southern, Jr. |
| 6,713,177 B2 | 3/2004 | George et al. |
| 6,715,541 B2 | 4/2004 | Pedersen et al. |
| 6,719,051 B2 | 4/2004 | Hailey, Jr. et al. |
| 6,755,249 B2 | 6/2004 | Robison et al. |
| 6,769,491 B2 | 8/2004 | Zimmerman et al. |
| 6,776,228 B2 | 8/2004 | Pedersen et al. |

(56) References Cited

U.S. PATENT DOCUMENTS

| | | |
|---|---|---|
| 6,779,599 B2 | 8/2004 | Mullins et al. |
| 6,799,638 B2 | 10/2004 | Butterfield, Jr. |
| 6,810,960 B2 | 11/2004 | Pia |
| 6,817,414 B2 | 11/2004 | Lee |
| 6,831,044 B2 | 12/2004 | Constien |
| 6,883,611 B2 | 4/2005 | Smith et al. |
| 6,887,297 B2 | 5/2005 | Winter et al. |
| 6,896,049 B2 | 5/2005 | Moyes |
| 6,896,061 B2 | 5/2005 | Hriscu et al. |
| 6,899,176 B2 | 5/2005 | Hailey, Jr. et al. |
| 6,899,777 B2 | 5/2005 | Vaidyanathan et al. |
| 6,908,516 B2 | 6/2005 | Hehmann et al. |
| 6,913,827 B2 | 7/2005 | George et al. |
| 6,926,086 B2 | 8/2005 | Patterson et al. |
| 6,932,159 B2 | 8/2005 | Hovem |
| 6,939,388 B2 | 9/2005 | Angeliu |
| 6,945,331 B2 | 9/2005 | Patel |
| 6,951,331 B2 | 10/2005 | Haughom et al. |
| 6,959,759 B2 | 11/2005 | Doane et al. |
| 6,973,970 B2 | 12/2005 | Johnston et al. |
| 6,973,973 B2 | 12/2005 | Howard et al. |
| 6,983,796 B2 | 1/2006 | Bayne et al. |
| 6,986,390 B2 | 1/2006 | Doane et al. |
| 7,013,989 B2 | 3/2006 | Hammond et al. |
| 7,013,998 B2 | 3/2006 | Ray et al. |
| 7,017,664 B2 | 3/2006 | Walker et al. |
| 7,017,677 B2 | 3/2006 | Keshavan et al. |
| 7,021,389 B2 | 4/2006 | Bishop et al. |
| 7,025,146 B2 | 4/2006 | King et al. |
| 7,028,778 B2 | 4/2006 | Krywitsky |
| 7,044,230 B2 | 5/2006 | Starr et al. |
| 7,049,272 B2 | 5/2006 | Sinclair et al. |
| 7,051,805 B2 | 5/2006 | Doane et al. |
| 7,059,410 B2 | 6/2006 | Bousche et al. |
| 7,090,027 B1 | 8/2006 | Williams |
| 7,093,664 B2 | 8/2006 | Todd et al. |
| 7,096,945 B2 | 8/2006 | Richards et al. |
| 7,096,946 B2 | 8/2006 | Jasser et al. |
| 7,097,906 B2 | 8/2006 | Gardner |
| 7,108,080 B2 | 9/2006 | Tessari et al. |
| 7,111,682 B2 | 9/2006 | Blaisdell |
| 7,128,145 B2 | 10/2006 | Mickey |
| 7,141,207 B2 | 11/2006 | Jandeska, Jr. et al. |
| 7,150,326 B2 | 12/2006 | Bishop et al. |
| 7,163,066 B2 | 1/2007 | Lehr |
| 7,165,622 B2 | 1/2007 | Hirth et al. |
| 7,168,494 B2 | 1/2007 | Starr et al. |
| 7,174,963 B2 | 2/2007 | Bertelsen |
| 7,182,135 B2 | 2/2007 | Szarka |
| 7,188,559 B1 | 3/2007 | Vecchio |
| 7,210,527 B2 | 5/2007 | Walker et al. |
| 7,210,533 B2 | 5/2007 | Starr et al. |
| 7,217,311 B2 | 5/2007 | Hong et al. |
| 7,234,530 B2 | 6/2007 | Gass |
| 7,250,188 B2 | 7/2007 | Dodelet et al. |
| 7,252,162 B2 | 8/2007 | Akinlade et al. |
| 7,255,172 B2 | 8/2007 | Johnson |
| 7,255,178 B2 | 8/2007 | Slup et al. |
| 7,264,060 B2 | 9/2007 | Wills |
| 7,267,172 B2 | 9/2007 | Hofman |
| 7,267,178 B2 | 9/2007 | Krywitsky |
| 7,270,186 B2 | 9/2007 | Johnson |
| 7,287,592 B2 | 10/2007 | Surjaatmadja et al. |
| 7,311,152 B2 | 12/2007 | Howard et al. |
| 7,316,274 B2 | 1/2008 | Xu et al. |
| 7,320,365 B2 | 1/2008 | Pia |
| 7,322,412 B2 | 1/2008 | Badalamenti et al. |
| 7,322,417 B2 | 1/2008 | Rytlewski et al. |
| 7,325,617 B2 | 2/2008 | Murray |
| 7,328,750 B2 | 2/2008 | Swor et al. |
| 7,331,388 B2 | 2/2008 | Vilela et al. |
| 7,337,854 B2 | 3/2008 | Horn et al. |
| 7,346,456 B2 | 3/2008 | Le Bemadjiel |
| 7,350,582 B2 | 4/2008 | McKeachnie et al. |
| 7,353,879 B2 | 4/2008 | Todd et al. |
| 7,360,593 B2 | 4/2008 | Constien |
| 7,360,597 B2 | 4/2008 | Blaisdell |
| 7,363,970 B2 | 4/2008 | Corre et al. |
| 7,373,978 B2 | 5/2008 | Barry et al. |
| 7,384,443 B2 | 6/2008 | Mirchandani |
| 7,387,158 B2 | 6/2008 | Murray et al. |
| 7,387,165 B2 | 6/2008 | Lopez De Cardenas et al. |
| 7,392,841 B2 | 7/2008 | Murray et al. |
| 7,401,648 B2 | 7/2008 | Bennett |
| 7,416,029 B2 | 8/2008 | Telfer et al. |
| 7,422,058 B2 | 9/2008 | O'Malley |
| 7,426,964 B2 | 9/2008 | Lynde et al. |
| 7,441,596 B2 | 10/2008 | Wood et al. |
| 7,445,049 B2 | 11/2008 | Howard et al. |
| 7,451,815 B2 | 11/2008 | Hailey, Jr. |
| 7,451,817 B2 | 11/2008 | Reddy et al. |
| 7,461,699 B2 | 12/2008 | Richard et al. |
| 7,464,764 B2 | 12/2008 | Xu |
| 7,472,750 B2 | 1/2009 | Walker et al. |
| 7,478,676 B2 | 1/2009 | East, Jr. et al. |
| 7,503,390 B2 | 3/2009 | Gomez |
| 7,503,399 B2 | 3/2009 | Badalamenti et al. |
| 7,509,993 B1 | 3/2009 | Turng et al. |
| 7,510,018 B2 | 3/2009 | Williamson et al. |
| 7,513,311 B2 | 4/2009 | Gramstad et al. |
| 7,527,103 B2 | 5/2009 | Huang et al. |
| 7,537,825 B1 | 5/2009 | Wardle et al. |
| 7,552,777 B2 | 6/2009 | Murray et al. |
| 7,552,779 B2 | 6/2009 | Murray |
| 7,559,357 B2 | 7/2009 | Clem |
| 7,575,062 B2 | 8/2009 | East, Jr. |
| 7,579,087 B2 | 8/2009 | Maloney et al. |
| 7,591,318 B2 | 9/2009 | Tilghman |
| 7,600,572 B2 | 10/2009 | Slup et al. |
| 7,604,049 B2 | 10/2009 | Vaidya et al. |
| 7,604,055 B2 | 10/2009 | Richard et al. |
| 7,607,476 B2 | 10/2009 | Tom et al. |
| 7,617,871 B2 | 11/2009 | Surjaatmadja et al. |
| 7,635,023 B2 | 12/2009 | Goldberg et al. |
| 7,640,988 B2 | 1/2010 | Phi et al. |
| 7,661,480 B2 | 2/2010 | Al-Anazi |
| 7,661,481 B2 | 2/2010 | Todd et al. |
| 7,665,537 B2 | 2/2010 | Patel et al. |
| 7,686,082 B2 | 3/2010 | Marsh |
| 7,690,436 B2 | 4/2010 | Turley et al. |
| 7,699,101 B2 | 4/2010 | Fripp et al. |
| 7,703,510 B2 | 4/2010 | Xu |
| 7,703,511 B2 | 4/2010 | Buyers et al. |
| 7,708,078 B2 | 5/2010 | Stoesz |
| 7,709,421 B2 | 5/2010 | Jones et al. |
| 7,712,541 B2 | 5/2010 | Loretz et al. |
| 7,723,272 B2 | 5/2010 | Crews et al. |
| 7,726,406 B2 | 6/2010 | Xu |
| 7,735,578 B2 | 6/2010 | Loehr et al. |
| 7,743,836 B2 | 6/2010 | Cook et al. |
| 7,752,971 B2 | 7/2010 | Loehr |
| 7,757,773 B2 | 7/2010 | Rytlewski |
| 7,762,342 B2 | 7/2010 | Richard et al. |
| 7,770,652 B2 | 8/2010 | Barnett |
| 7,775,284 B2 | 8/2010 | Richards et al. |
| 7,775,285 B2 | 8/2010 | Surjaatmadja et al. |
| 7,775,286 B2 | 8/2010 | Duphorne |
| 7,784,543 B2 | 8/2010 | Johnson |
| 7,793,714 B2 | 9/2010 | Johnson |
| 7,793,820 B2 | 9/2010 | Hirano et al. |
| 7,798,225 B2 | 9/2010 | Giroux et al. |
| 7,798,226 B2 | 9/2010 | Themig |
| 7,798,236 B2 | 9/2010 | McKeachnie et al. |
| 7,806,189 B2 | 10/2010 | Frazier |
| 7,806,192 B2 | 10/2010 | Foster et al. |
| 7,810,553 B2 | 10/2010 | Cruickshank et al. |
| 7,810,567 B2 | 10/2010 | Daniels et al. |
| 7,819,198 B2 | 10/2010 | Birckhead et al. |
| 7,828,055 B2 | 11/2010 | Willauer et al. |
| 7,833,944 B2 | 11/2010 | Munoz et al. |
| 7,849,927 B2 | 12/2010 | Herrera |
| 7,851,016 B2 | 12/2010 | Arbab et al. |
| 7,855,168 B2 | 12/2010 | Fuller et al. |
| 7,861,779 B2 | 1/2011 | Vestavik |

(56) References Cited

U.S. PATENT DOCUMENTS

| | | |
|---|---|---|
| 7,861,781 B2 | 1/2011 | D'Arcy |
| 7,874,365 B2 | 1/2011 | East, Jr. et al. |
| 7,878,253 B2 | 2/2011 | Stowe et al. |
| 7,896,091 B2 | 3/2011 | Williamson et al. |
| 7,897,063 B1 | 3/2011 | Perry et al. |
| 7,900,696 B1 | 3/2011 | Nish et al. |
| 7,900,703 B2 | 3/2011 | Clark et al. |
| 7,909,096 B2 | 3/2011 | Clark et al. |
| 7,909,104 B2 | 3/2011 | Bjorgum |
| 7,909,110 B2 | 3/2011 | Sharma et al. |
| 7,909,115 B2 | 3/2011 | Grove et al. |
| 7,913,765 B2 | 3/2011 | Crow et al. |
| 7,918,275 B2 | 4/2011 | Clem |
| 7,931,093 B2 | 4/2011 | Foster et al. |
| 7,938,191 B2 | 5/2011 | Vaidya |
| 7,946,335 B2 | 5/2011 | Bewlay et al. |
| 7,946,340 B2 | 5/2011 | Surjaatmadja et al. |
| 7,958,940 B2 | 6/2011 | Jameson |
| 7,963,331 B2 | 6/2011 | Surjaatmadja et al. |
| 7,963,340 B2 | 6/2011 | Gramstad et al. |
| 7,963,342 B2 | 6/2011 | George |
| 7,980,300 B2 | 7/2011 | Roberts et al. |
| 7,987,906 B1 | 8/2011 | Troy |
| 7,992,763 B2 | 8/2011 | Vecchio et al. |
| 8,020,619 B1 | 9/2011 | Robertson et al. |
| 8,020,620 B2 | 9/2011 | Daniels et al. |
| 8,025,104 B2 | 9/2011 | Cooke, Jr. |
| 8,028,767 B2 | 10/2011 | Radford et al. |
| 8,033,331 B2 | 10/2011 | Themig |
| 8,039,422 B1 | 10/2011 | Al-Zahrani |
| 8,056,628 B2 | 11/2011 | Whitsitt et al. |
| 8,056,638 B2 | 11/2011 | Clayton et al. |
| 8,109,340 B2 | 2/2012 | Doane et al. |
| 8,127,856 B1 | 3/2012 | Nish et al. |
| 8,153,052 B2 | 4/2012 | Jackson et al. |
| 8,163,060 B2 | 4/2012 | Imanishi et al. |
| 8,211,247 B2 | 7/2012 | Marya et al. |
| 8,211,248 B2 | 7/2012 | Marya |
| 8,226,740 B2 | 7/2012 | Chaumonnot et al. |
| 8,230,731 B2 | 7/2012 | Dyer et al. |
| 8,231,947 B2 | 7/2012 | Vaidya et al. |
| 8,263,178 B2 | 9/2012 | Boulos et al. |
| 8,276,670 B2 | 10/2012 | Patel |
| 8,277,974 B2 | 10/2012 | Kumar et al. |
| 8,297,364 B2 | 10/2012 | Agrawal et al. |
| 8,327,931 B2 | 12/2012 | Agrawal et al. |
| 8,403,037 B2 | 3/2013 | Agrawal et al. |
| 8,425,651 B2 | 4/2013 | Xu et al. |
| 8,459,347 B2 | 6/2013 | Stout |
| 8,490,689 B1 | 7/2013 | McClinton et al. |
| 8,535,604 B1 | 9/2013 | Baker et al. |
| 8,573,295 B2 | 11/2013 | Johnson et al. |
| 8,631,876 B2 | 1/2014 | Xu et al. |
| 8,956,660 B2 | 2/2015 | Launag et al. |
| 9,079,246 B2 | 7/2015 | Xu et al. |
| 9,080,098 B2 | 7/2015 | Xu et al. |
| 9,260,935 B2 | 2/2016 | Murphree et al. |
| 2001/0040180 A1 | 11/2001 | Wittebrood et al. |
| 2001/0045285 A1 | 11/2001 | Russell |
| 2001/0045288 A1 | 11/2001 | Allamon et al. |
| 2002/0000319 A1 | 1/2002 | Brunet |
| 2002/0007948 A1 | 1/2002 | Bayne et al. |
| 2002/0014268 A1 | 2/2002 | Vann |
| 2002/0020527 A1* | 2/2002 | Kilaas ............... B01D 39/1653 166/250.01 |
| 2002/0066572 A1 | 6/2002 | Muth |
| 2002/0092654 A1 | 7/2002 | Coronado et al. |
| 2002/0096365 A1 | 7/2002 | Berscheidt et al. |
| 2002/0104616 A1 | 8/2002 | De et al. |
| 2002/0108756 A1 | 8/2002 | Harrall et al. |
| 2002/0136904 A1 | 9/2002 | Glass et al. |
| 2002/0139541 A1 | 10/2002 | Sheffield et al. |
| 2002/0162661 A1 | 11/2002 | Krauss et al. |
| 2003/0019639 A1 | 1/2003 | Mackay |
| 2003/0037925 A1 | 2/2003 | Walker et al. |
| 2003/0060374 A1 | 3/2003 | Cooke, Jr. |
| 2003/0075326 A1 | 4/2003 | Ebinger |
| 2003/0104147 A1 | 6/2003 | Bretschneider et al. |
| 2003/0111728 A1 | 6/2003 | Thai et al. |
| 2003/0127013 A1 | 7/2003 | Zavitsanos et al. |
| 2003/0141060 A1 | 7/2003 | Hailey et al. |
| 2003/0141061 A1 | 7/2003 | Hailey et al. |
| 2003/0141079 A1 | 7/2003 | Doane et al. |
| 2003/0150614 A1 | 8/2003 | Brown et al. |
| 2003/0155114 A1 | 8/2003 | Pedersen et al. |
| 2003/0155115 A1 | 8/2003 | Pedersen et al. |
| 2003/0159828 A1 | 8/2003 | Howard et al. |
| 2003/0164237 A1 | 9/2003 | Butterfield |
| 2003/0183391 A1 | 10/2003 | Hriscu et al. |
| 2003/0226668 A1 | 12/2003 | Zimmerman et al. |
| 2004/0005483 A1 | 1/2004 | Lin |
| 2004/0020832 A1 | 2/2004 | Richards et al. |
| 2004/0031605 A1 | 2/2004 | Mickey |
| 2004/0045723 A1 | 3/2004 | Slup et al. |
| 2004/0055758 A1 | 3/2004 | Brezinski et al. |
| 2004/0058167 A1 | 3/2004 | Arbab et al. |
| 2004/0069502 A1 | 4/2004 | Luke |
| 2004/0089449 A1 | 5/2004 | Walton et al. |
| 2004/0094297 A1* | 5/2004 | Malone ............... E21B 47/1015 166/250.12 |
| 2004/0154806 A1 | 8/2004 | Bode et al. |
| 2004/0159428 A1 | 8/2004 | Hammond et al. |
| 2004/0159446 A1 | 8/2004 | Haugen et al. |
| 2004/0182583 A1 | 9/2004 | Doane et al. |
| 2004/0216868 A1 | 11/2004 | Owen, Sr. |
| 2004/0231845 A1 | 11/2004 | Cooke, Jr. |
| 2004/0251025 A1 | 12/2004 | Giroux et al. |
| 2004/0256109 A1 | 12/2004 | Johnson |
| 2004/0256157 A1 | 12/2004 | Tessari |
| 2004/0261993 A1 | 12/2004 | Nguyen |
| 2004/0261994 A1 | 12/2004 | Nguyen et al. |
| 2005/0034876 A1 | 2/2005 | Doane et al. |
| 2005/0051329 A1 | 3/2005 | Blaisdell |
| 2005/0064247 A1 | 3/2005 | Sane et al. |
| 2005/0069449 A1 | 3/2005 | Jackson et al. |
| 2005/0074612 A1 | 4/2005 | Eklund et al. |
| 2005/0098313 A1 | 5/2005 | Atkins et al. |
| 2005/0102255 A1 | 5/2005 | Bultman |
| 2005/0106316 A1 | 5/2005 | Rigney et al. |
| 2005/0126334 A1 | 6/2005 | Mirchandani |
| 2005/0161212 A1 | 7/2005 | Leismer et al. |
| 2005/0161224 A1 | 7/2005 | Starr et al. |
| 2005/0165149 A1 | 7/2005 | Chanak et al. |
| 2005/0194143 A1 | 9/2005 | Xu et al. |
| 2005/0199401 A1 | 9/2005 | Patel et al. |
| 2005/0205264 A1 | 9/2005 | Starr et al. |
| 2005/0205265 A1 | 9/2005 | Todd et al. |
| 2005/0205266 A1 | 9/2005 | Todd et al. |
| 2005/0235757 A1 | 10/2005 | De Jonge et al. |
| 2005/0241824 A1 | 11/2005 | Burris, II et al. |
| 2005/0241825 A1 | 11/2005 | Burris, II et al. |
| 2005/0257936 A1 | 11/2005 | Lehr |
| 2005/0268746 A1 | 12/2005 | Abkowitz et al. |
| 2005/0269097 A1 | 12/2005 | Yowler |
| 2005/0275143 A1 | 12/2005 | Toth |
| 2005/0279501 A1 | 12/2005 | Surjaatmadja et al. |
| 2006/0012087 A1 | 1/2006 | Matsuda et al. |
| 2006/0013350 A1* | 1/2006 | Akers ............... G01N 23/227 376/156 |
| 2006/0045787 A1 | 3/2006 | Jandeska et al. |
| 2006/0057479 A1 | 3/2006 | Niimi et al. |
| 2006/0081378 A1 | 4/2006 | Howard et al. |
| 2006/0102871 A1 | 5/2006 | Wang |
| 2006/0108114 A1 | 5/2006 | Johnson et al. |
| 2006/0108126 A1 | 5/2006 | Horn et al. |
| 2006/0110615 A1 | 5/2006 | Karim et al. |
| 2006/0116696 A1 | 6/2006 | Odermatt et al. |
| 2006/0124310 A1 | 6/2006 | Lopez De Cardenas et al. |
| 2006/0131011 A1 | 6/2006 | Lynde et al. |
| 2006/0131031 A1 | 6/2006 | McKeachnie et al. |
| 2006/0131081 A1 | 6/2006 | Mirchandani et al. |
| 2006/0134312 A1 | 6/2006 | Rytlewski et al. |
| 2006/0144515 A1 | 7/2006 | Tada et al. |
| 2006/0150770 A1 | 7/2006 | Freim |

(56) References Cited

U.S. PATENT DOCUMENTS

| | | |
|---|---|---|
| 2006/0151178 A1 | 7/2006 | Howard et al. |
| 2006/0153728 A1 | 7/2006 | Schoenung et al. |
| 2006/0162927 A1 | 7/2006 | Walker et al. |
| 2006/0169453 A1 | 8/2006 | Savery et al. |
| 2006/0186602 A1 | 8/2006 | Martin et al. |
| 2006/0207763 A1 | 9/2006 | Hofman et al. |
| 2006/0213670 A1 | 9/2006 | Bishop et al. |
| 2006/0231253 A1 | 10/2006 | Vilela et al. |
| 2006/0283592 A1 | 12/2006 | Sierra et al. |
| 2007/0017674 A1 | 1/2007 | Blaisdell |
| 2007/0017675 A1 | 1/2007 | Hammami |
| 2007/0029082 A1 | 2/2007 | Giroux et al. |
| 2007/0039161 A1 | 2/2007 | Garcia |
| 2007/0039741 A1 | 2/2007 | Hailey |
| 2007/0044958 A1 | 3/2007 | Rytlewski et al. |
| 2007/0044966 A1 | 3/2007 | Davies et al. |
| 2007/0051521 A1 | 3/2007 | Fike et al. |
| 2007/0053785 A1 | 3/2007 | Hetz et al. |
| 2007/0054101 A1 | 3/2007 | Sigalas et al. |
| 2007/0057415 A1 | 3/2007 | Katagiri et al. |
| 2007/0062644 A1 | 3/2007 | Nakamura et al. |
| 2007/0074601 A1 | 4/2007 | Hong et al. |
| 2007/0074873 A1 | 4/2007 | McKeachnie et al. |
| 2007/0102199 A1 | 5/2007 | Smith et al. |
| 2007/0107899 A1 | 5/2007 | Werner et al. |
| 2007/0107908 A1 | 5/2007 | Vaidya et al. |
| 2007/0108060 A1 | 5/2007 | Park |
| 2007/0119600 A1 | 5/2007 | Slup et al. |
| 2007/0131912 A1 | 6/2007 | Simone et al. |
| 2007/0151009 A1 | 7/2007 | Conrad, III et al. |
| 2007/0151769 A1 | 7/2007 | Slutz et al. |
| 2007/0169935 A1 | 7/2007 | Akbar et al. |
| 2007/0181224 A1 | 8/2007 | Marya et al. |
| 2007/0185655 A1 | 8/2007 | Le Bemadjiel |
| 2007/0187095 A1 | 8/2007 | Walker et al. |
| 2007/0207182 A1 | 9/2007 | Weber et al. |
| 2007/0221373 A1 | 9/2007 | Murray |
| 2007/0221384 A1 | 9/2007 | Murray |
| 2007/0227745 A1 | 10/2007 | Roberts et al. |
| 2007/0259994 A1 | 11/2007 | Tour et al. |
| 2007/0261862 A1 | 11/2007 | Murray |
| 2007/0272411 A1 | 11/2007 | Lopez De Cardenas et al. |
| 2007/0272413 A1 | 11/2007 | Rytlewski et al. |
| 2007/0277979 A1 | 12/2007 | Todd et al. |
| 2007/0284109 A1 | 12/2007 | East et al. |
| 2007/0284112 A1 | 12/2007 | Magne et al. |
| 2007/0299510 A1 | 12/2007 | Venkatraman et al. |
| 2008/0011473 A1 | 1/2008 | Wood et al. |
| 2008/0020923 A1 | 1/2008 | Debe et al. |
| 2008/0047707 A1 | 2/2008 | Boney et al. |
| 2008/0060810 A9 | 3/2008 | Nguyen et al. |
| 2008/0066923 A1 | 3/2008 | Xu |
| 2008/0066924 A1 | 3/2008 | Xu |
| 2008/0072705 A1 | 3/2008 | Chaumonnot et al. |
| 2008/0078553 A1 | 4/2008 | George |
| 2008/0081866 A1 | 4/2008 | Gong et al. |
| 2008/0093073 A1 | 4/2008 | Bustos et al. |
| 2008/0099209 A1 | 5/2008 | Loretz et al. |
| 2008/0105438 A1 | 5/2008 | Jordan et al. |
| 2008/0115932 A1 | 5/2008 | Cooke |
| 2008/0121390 A1 | 5/2008 | O3 Malley et al. |
| 2008/0121436 A1 | 5/2008 | Slay et al. |
| 2008/0127475 A1 | 6/2008 | Griffo |
| 2008/0135249 A1 | 6/2008 | Fripp et al. |
| 2008/0149325 A1 | 6/2008 | Crawford |
| 2008/0149345 A1 | 6/2008 | Bicerano |
| 2008/0149351 A1 | 6/2008 | Marya et al. |
| 2008/0169105 A1 | 7/2008 | Williamson et al. |
| 2008/0169130 A1 | 7/2008 | Norman et al. |
| 2008/0179060 A1 | 7/2008 | Surjaatmadja et al. |
| 2008/0179104 A1 | 7/2008 | Zhang et al. |
| 2008/0196801 A1 | 8/2008 | Zhao et al. |
| 2008/0202764 A1 | 8/2008 | Clayton et al. |
| 2008/0202814 A1 | 8/2008 | Lyons et al. |
| 2008/0210473 A1 | 9/2008 | Zhang et al. |
| 2008/0216383 A1 | 9/2008 | Pierick et al. |
| 2008/0223586 A1 | 9/2008 | Barnett |
| 2008/0223587 A1 | 9/2008 | Cherewyk |
| 2008/0236829 A1 | 10/2008 | Lynde |
| 2008/0236842 A1 | 10/2008 | Bhavsar et al. |
| 2008/0248205 A1 | 10/2008 | Blanchet et al. |
| 2008/0248413 A1 | 10/2008 | Ishii et al. |
| 2008/0264594 A1 | 10/2008 | Lohmueller et al. |
| 2008/0277109 A1 | 11/2008 | Vaidya |
| 2008/0277980 A1 | 11/2008 | Koda et al. |
| 2008/0282924 A1 | 11/2008 | Saenger et al. |
| 2008/0296024 A1 | 12/2008 | Tianping et al. |
| 2008/0302538 A1 | 12/2008 | Hofman |
| 2008/0314581 A1 | 12/2008 | Brown |
| 2008/0314588 A1 | 12/2008 | Langlais et al. |
| 2009/0038858 A1 | 2/2009 | Griffo et al. |
| 2009/0044946 A1 | 2/2009 | Schasteen et al. |
| 2009/0044949 A1 | 2/2009 | King et al. |
| 2009/0050334 A1 | 2/2009 | Marya et al. |
| 2009/0056934 A1 | 3/2009 | Xu |
| 2009/0065216 A1 | 3/2009 | Frazier |
| 2009/0074603 A1 | 3/2009 | Chan et al. |
| 2009/0084553 A1 | 4/2009 | Rytlewski et al. |
| 2009/0084556 A1 | 4/2009 | Richards et al. |
| 2009/0084600 A1 | 4/2009 | Severance |
| 2009/0090440 A1 | 4/2009 | Kellett et al. |
| 2009/0107684 A1 | 4/2009 | Cooke, Jr. |
| 2009/0114381 A1 | 5/2009 | Stroobants |
| 2009/0114382 A1 | 5/2009 | Grove et al. |
| 2009/0126436 A1 | 5/2009 | Fly et al. |
| 2009/0139720 A1 | 6/2009 | Frazier |
| 2009/0145666 A1 | 6/2009 | Radford et al. |
| 2009/0151949 A1 | 6/2009 | Marya et al. |
| 2009/0152009 A1 | 6/2009 | Slay et al. |
| 2009/0155616 A1 | 6/2009 | Thamida et al. |
| 2009/0159289 A1 | 6/2009 | Avant et al. |
| 2009/0178808 A1 | 7/2009 | Williamson et al. |
| 2009/0194273 A1 | 8/2009 | Surjaatmadja et al. |
| 2009/0205841 A1 | 8/2009 | Kluge et al. |
| 2009/0211770 A1 | 8/2009 | Nutley et al. |
| 2009/0226340 A1 | 9/2009 | Marya |
| 2009/0226704 A1 | 9/2009 | Kauppinen et al. |
| 2009/0242202 A1 | 10/2009 | Rispler et al. |
| 2009/0242208 A1 | 10/2009 | Bolding |
| 2009/0242214 A1 | 10/2009 | Foster et al. |
| 2009/0255667 A1 | 10/2009 | Clem et al. |
| 2009/0255684 A1 | 10/2009 | Bolding |
| 2009/0255686 A1 | 10/2009 | Richard |
| 2009/0266548 A1 | 10/2009 | Olsen et al. |
| 2009/0260817 A1 | 11/2009 | Gambier et al. |
| 2009/0272544 A1 | 11/2009 | Giroux et al. |
| 2009/0283270 A1 | 11/2009 | Langeslag |
| 2009/0293672 A1 | 12/2009 | Mirchandani et al. |
| 2009/0301730 A1 | 12/2009 | Gweily |
| 2009/0305131 A1 | 12/2009 | Kumar et al. |
| 2009/0308588 A1 | 12/2009 | Howell et al. |
| 2009/0317556 A1 | 12/2009 | Macary |
| 2009/0317622 A1 | 12/2009 | Huang et al. |
| 2010/0003536 A1 | 1/2010 | Smith et al. |
| 2010/0012385 A1 | 1/2010 | Drivdahl et al. |
| 2010/0015002 A1 | 1/2010 | Barrera et al. |
| 2010/0015469 A1 | 1/2010 | Romanowski et al. |
| 2010/0025255 A1 | 2/2010 | Su et al. |
| 2010/0032151 A1 | 2/2010 | Duphorne et al. |
| 2010/0034857 A1 | 2/2010 | Launag et al. |
| 2010/0038076 A1 | 2/2010 | Spray et al. |
| 2010/0038595 A1 | 2/2010 | Imholt et al. |
| 2010/0040180 A1 | 2/2010 | Kim et al. |
| 2010/0044041 A1 | 2/2010 | Smith et al. |
| 2010/0051278 A1 | 3/2010 | Mytopher et al. |
| 2010/0055491 A1 | 3/2010 | Vecchio et al. |
| 2010/0055492 A1 | 3/2010 | Barsoum et al. |
| 2010/0089583 A1 | 4/2010 | Xu et al. |
| 2010/0089587 A1 | 4/2010 | Stout |
| 2010/0101803 A1 | 4/2010 | Clayton et al. |
| 2010/0116495 A1 | 5/2010 | Spray |
| 2010/0122817 A1 | 5/2010 | Surjaatmadja et al. |
| 2010/0139930 A1 | 6/2010 | Patel et al. |
| 2010/0200230 A1 | 8/2010 | East, Jr. et al. |

(56) References Cited

U.S. PATENT DOCUMENTS

| | | |
|---|---|---|
| 2010/0236793 A1 | 9/2010 | Bjorgum |
| 2010/0236794 A1 | 9/2010 | Duan et al. |
| 2010/0243254 A1 | 9/2010 | Murphy et al. |
| 2010/0252273 A1 | 10/2010 | Duphorne |
| 2010/0252280 A1 | 10/2010 | Swor et al. |
| 2010/0270031 A1 | 10/2010 | Patel |
| 2010/0276136 A1 | 11/2010 | Evans et al. |
| 2010/0276159 A1 | 11/2010 | Mailand et al. |
| 2010/0282338 A1 | 11/2010 | Gerrard et al. |
| 2010/0282469 A1 | 11/2010 | Richard et al. |
| 2010/0294510 A1 | 11/2010 | Holmes |
| 2010/0297432 A1 | 11/2010 | Sherman et al. |
| 2010/0314105 A1* | 12/2010 | Rose .............. E21B 43/26 166/250.1 |
| 2010/0314126 A1 | 12/2010 | Kellner |
| 2010/0319870 A1 | 12/2010 | Bewlay et al. |
| 2010/0326650 A1 | 12/2010 | Tran et al. |
| 2011/0005773 A1 | 1/2011 | Dusterhoft et al. |
| 2011/0036592 A1 | 2/2011 | Fay |
| 2011/0048743 A1 | 3/2011 | Stafford et al. |
| 2011/0052805 A1 | 3/2011 | Bordere et al. |
| 2011/0056692 A1 | 3/2011 | Lopez De Cardenas et al. |
| 2011/0056702 A1 | 3/2011 | Sharma et al. |
| 2011/0067872 A1 | 3/2011 | Agrawal |
| 2011/0067889 A1 | 3/2011 | Marya et al. |
| 2011/0067890 A1 | 3/2011 | Themig |
| 2011/0094406 A1 | 4/2011 | Marya et al. |
| 2011/0100643 A1 | 5/2011 | Themig et al. |
| 2011/0127044 A1 | 6/2011 | Radford et al. |
| 2011/0132143 A1 | 6/2011 | Xu et al. |
| 2011/0132612 A1 | 6/2011 | Agrawal et al. |
| 2011/0132619 A1 | 6/2011 | Agrawal et al. |
| 2011/0132620 A1 | 6/2011 | Agrawal et al. |
| 2011/0132621 A1 | 6/2011 | Agrawal et al. |
| 2011/0135530 A1 | 6/2011 | Xu et al. |
| 2011/0135805 A1 | 6/2011 | Doucet et al. |
| 2011/0135953 A1 | 6/2011 | Xu et al. |
| 2011/0136707 A1 | 6/2011 | Xu et al. |
| 2011/0139465 A1 | 6/2011 | Tibbles et al. |
| 2011/0147014 A1 | 6/2011 | Chen et al. |
| 2011/0186306 A1 | 8/2011 | Marya et al. |
| 2011/0214881 A1 | 9/2011 | Newton |
| 2011/0247833 A1 | 10/2011 | Todd et al. |
| 2011/0253387 A1 | 10/2011 | Ervin |
| 2011/0256356 A1 | 10/2011 | Tomantschger et al. |
| 2011/0259610 A1 | 10/2011 | Shkurti et al. |
| 2011/0277987 A1 | 11/2011 | Frazier |
| 2011/0277989 A1 | 11/2011 | Frazier |
| 2011/0277996 A1* | 11/2011 | Cullick ............ E21B 33/138 166/250.12 |
| 2011/0284232 A1 | 11/2011 | Huang |
| 2011/0284240 A1 | 11/2011 | Chen et al. |
| 2011/0284243 A1 | 11/2011 | Frazier |
| 2011/0300403 A1 | 12/2011 | Vecchio et al. |
| 2011/0314881 A1 | 12/2011 | Hatcher et al. |
| 2012/0024109 A1* | 2/2012 | Xu .............. B22F 1/025 75/243 |
| 2012/0067426 A1 | 3/2012 | Soni et al. |
| 2012/0090839 A1 | 4/2012 | Rudic |
| 2012/0103135 A1 | 5/2012 | Xu et al. |
| 2012/0107590 A1 | 5/2012 | Xu et al. |
| 2012/0118583 A1 | 5/2012 | Johnson et al. |
| 2012/0130470 A1 | 5/2012 | Agnew |
| 2012/0145378 A1 | 6/2012 | Frazier et al. |
| 2012/0145389 A1 | 6/2012 | Fitzpatrick, Jr. |
| 2012/0168152 A1 | 7/2012 | Casciaro et al. |
| 2012/0177905 A1 | 7/2012 | Seals et al. |
| 2012/0205120 A1 | 8/2012 | Howell |
| 2012/0205872 A1 | 8/2012 | Reinhardt et al. |
| 2012/0211239 A1 | 8/2012 | Kritzler et al. |
| 2012/0234546 A1 | 9/2012 | Xu et al. |
| 2012/0234547 A1 | 9/2012 | O'Malley et al. |
| 2012/0267101 A1 | 10/2012 | Cooke |
| 2012/0292053 A1 | 11/2012 | Xu et al. |
| 2012/0318513 A1 | 12/2012 | Mazyar et al. |
| 2013/0004847 A1 | 1/2013 | Kumar et al. |
| 2013/0008671 A1 | 1/2013 | Booth et al. |
| 2013/0017610 A1* | 1/2013 | Roberts .............. C09K 11/06 436/27 |
| 2013/0025409 A1 | 1/2013 | Xu |
| 2013/0029886 A1 | 1/2013 | Mazyar et al. |
| 2013/0032357 A1 | 2/2013 | Mazyar et al. |
| 2013/0048304 A1 | 2/2013 | Agrawal et al. |
| 2013/0048305 A1 | 2/2013 | Xu et al. |
| 2013/0052472 A1 | 2/2013 | Xu |
| 2013/0081814 A1 | 4/2013 | Gaudette et al. |
| 2013/0084643 A1* | 4/2013 | Commarieu .............. C09K 8/03 436/27 |
| 2013/0105159 A1 | 5/2013 | Alvarez |
| 2013/0126190 A1 | 5/2013 | Mazyar et al. |
| 2013/0133897 A1 | 5/2013 | Baihly et al. |
| 2013/0146144 A1 | 6/2013 | Joseph et al. |
| 2013/0146302 A1 | 6/2013 | Gaudette et al. |
| 2013/0168257 A1 | 7/2013 | Mazyar et al. |
| 2013/0186626 A1 | 7/2013 | Aitken et al. |
| 2013/0240200 A1 | 9/2013 | Frazier |
| 2013/0240203 A1 | 9/2013 | Frazier |
| 2013/0299185 A1* | 11/2013 | Xu .............. E21B 43/106 166/376 |
| 2013/0299192 A1 | 11/2013 | Xu et al. |
| 2013/0300066 A1 | 11/2013 | Xu et al. |
| 2013/0319668 A1 | 12/2013 | Tschetter et al. |
| 2013/0327540 A1 | 12/2013 | Hamid et al. |
| 2014/0014339 A1* | 1/2014 | O'Malley ............ E21B 43/261 166/281 |
| 2014/0027128 A1 | 1/2014 | Johnson et al. |
| 2014/0060834 A1 | 3/2014 | Quintero et al. |
| 2014/0116711 A1 | 5/2014 | Tang et al. |
| 2014/0262327 A1 | 9/2014 | Xu et al. |
| 2014/0360728 A1 | 12/2014 | Tashiro et al. |
| 2015/0060085 A1 | 3/2015 | Xu |
| 2016/0272882 A1* | 9/2016 | Stray .............. C09K 8/03 |

FOREIGN PATENT DOCUMENTS

| | | |
|---|---|---|
| CN | 1076968 A | 10/1993 |
| CN | 1079234 A | 12/1993 |
| CN | 1255879 A | 6/2000 |
| CN | 1668545 A | 9/2005 |
| CN | 1882759 A1 | 12/2006 |
| CN | 101050417 A | 10/2007 |
| CN | 101351523 A | 1/2009 |
| CN | 101454074 A | 6/2009 |
| CN | 101457321 A | 6/2009 |
| EP | 0033625 A1 | 8/1981 |
| EP | 1174385 A2 | 1/2002 |
| EP | 1412175 A1 | 4/2004 |
| EP | 1798301 A1 | 8/2006 |
| EP | 1857570 A2 | 11/2007 |
| FR | 2782096 A1 | 2/2000 |
| GB | 912956 A | 12/1962 |
| GB | 1046330 A | 10/1966 |
| GB | 1280833 A | 7/1972 |
| GB | 1357065 A | 6/1974 |
| JP | 61067770 A | 4/1986 |
| JP | 754008 A | 2/1995 |
| JP | 8232029 A | 9/1996 |
| JP | 2000185725 A1 | 7/2000 |
| JP | 2002053902 A | 2/2002 |
| JP | 2004225084 A | 8/2004 |
| JP | 2004225765 A | 8/2004 |
| JP | 2005076052 A | 3/2005 |
| JP | 2010502840 A | 1/2010 |
| KR | 950014350 B1 | 11/1995 |
| WO | 9909227 A1 | 2/1999 |
| WO | 9947726 A1 | 9/1999 |
| WO | 03008186 A1 | 1/2003 |
| WO | 2004001087 A1 | 12/2003 |
| WO | 2004073889 A1 | 9/2004 |
| WO | 2005040068 A | 5/2005 |
| WO | 2007044635 A | 4/2007 |
| WO | 2007095376 A2 | 8/2007 |
| WO | 2008034042 A3 | 3/2008 |

(56) References Cited

FOREIGN PATENT DOCUMENTS

| | | | |
|---|---|---|---|
| WO | 2008057045 A1 | 5/2008 | |
| WO | 2008079485 A2 | 7/2008 | |
| WO | 2008079777 A2 | 7/2008 | |
| WO | 2009079745 A1 | 7/2009 | |
| WO | 2010012184 A1 | 2/2010 | |
| WO | 2011071902 A2 | 6/2011 | |
| WO | 2011071910 A2 | 6/2011 | |
| WO | 2011130063 A3 | 2/2012 | |
| WO | 2012015567 A2 | 2/2012 | |
| WO | 2012149007 A2 | 11/2012 | |
| WO | 2012174101 A2 | 12/2012 | |
| WO | WO 2012175665 A1 * | 12/2012 | .......... B01J 13/0039 |
| WO | 2013053057 A1 | 4/2013 | |
| WO | 2013078031 A1 | 5/2013 | |
| WO | 2014121384 A1 | 8/2014 | |

OTHER PUBLICATIONS

European Search Report for EP Application No. 12827733.2 dated Jan. 21, 2015.
European Search Report for EP Application No. 12827915.5 dated Dec. 23, 2015.
European Search Report for EP Application No. 12828903.0 dated Jan. 11, 2016.
Extended European Search Report for EP Application No. 12828379.3-1373, dated May 20, 2016, 8 pages.
International Search Report and Written Opinion; International Application No. PCT/US2015/066353; International Filing Date: Dec. 17, 2015; dated Apr. 1, 2016; 14 pages.
Canadian Office Action for Canadian Application No. 2,841,068, dated Nov. 9, 2015, pp. 1-4.
Extended European Search Report; EP Application No. 12822169.4-1605/2739812; Dated: Nov. 17, 2015; 9 pages.
European Search Report for EP Application No. 10836533.9 dated Jul. 27, 2015.
Australian Examination Report for Australian patent application No. 2012302067 dated Sep. 22, 2015.
Australian Examination Report; Australian Application No. 2012287461; Dated: Jul. 13, 2015; 6 pages.
Chinese Office Action for Chinese Application No. 201280036477.4, dated Nov. 4, 2015, pp. 1-15.
Chinese Office Action; Chinese Application No. 201280020572.5; Dated: Oct. 10, 2015; 13 pages.
Chuan-Jun et al., "Study on Corrosion Kinetics of Mg—Ni alloys", Journal of Kunming University of Science and Technology, vol. 34, No. 5, pp. Oct. 10-13, 2009.
European Search Report for EP Application No. 10836538.8 dated Jul. 27, 2015.
European Search Report for EP Application No. 10836540.4 dated Aug. 20, 2015.
European Search Report for EP Application No. 10836539.6 dated Jul. 27, 2015.
Tsipas et al. "Effect of High Energy Ball Milling on Titanium-Hydroxyapatite Powders" Powder Metallurgy, Maney Publishing, London, GB, vol. 46, No. 1, Mar. 2003 (Mar. 2003), pp. 73-77.
Chinese Office Action; Chinese Application No. 201280041839.9; Dated: Feb. 10, 2015; pp. 1-37.
Chinese Office Action; Chinese Application No. 201280041320.0; Dated: May 11, 2015; pp. 1-17.
"Sliding Sleeve", Omega Completion Technology Ltd, Sep. 29, 2009, retrieved on: www.omega-completion.com.
Ambat, et al., "Electroless Nickel-Plating on AZ91D Magnesium Alloy: Effect of Substrate Microstructure and Plating Parameters"; Surface and Coatings Technology; 179; pp. 124-134; (2004).
Baker Oil Tools, "Baker Oil Tools Introduces Revolutionary Sand Control Completion Technology," May 2, 2005.
Baker Oil Tools, "Z-Seal Metal-to-Metal Expandable Sealing Device Uses Expanding Metal in Place of Elastomers," Nov. 6, 2006.

Bastow, et al., "Clustering and formation of nano-precipitates in dilute aluminum and magnesium alloys", Materials Science and Engineering, 2003, C23, 757-762.
Bercegeay, et al., "A One-Trip Gravel Packing System"; Society of Petroleum Engineers, Offshort Technology Conference, SPE Paper No. 4771; Feb. 7-8, 1974.
Bybee, "One-Trip Completion System Eliminates Perforations," Completions Today, Sep. 2007, pp. 52-53.
Canadian Office Action for Canadian Application No. 2,783,547, dated Feb. 15, 2013, pp. 1-3.
Chang, et al., "Electrodeposition of Aluminum on Magnesium Alloy in Aluminum Chloride (AlC13)-1-ethyl-3-methylimidazolium chloride (EMIC) Ionic Liquid and Its Corrosion Behavior"; Electrochemistry Communications; 9; pp. 1602-1606; (2007).
Christoglou, et al., "Deposition of Aluminum on Magnesium by a CVD Process", Surface and Coatings Technology 184 (2004) 149-155.
Constantine, "Selective Production of Horizontal Openhole Completions Using ECP and Sliding Sleeve Technology." SPE Rocky Mountain Regional Meeting, May 15-18, 1999, Gillette, Wyoming. [Abstract Only].
Curtin, et al., "CNT-reinforced ceramics and metals," Materials Today, 2004, vol. 7, pp. 44-49.
Flahaut, et al., "Carbon Nanotube-Metal-Oxide Nanocomposites: Microstructure, Electrical Conductivity and Mechanical Properties" Acta amter. 48 (2000), pp. 3803-3812.
Forsyth, et al.; "An Ionic Liquid Surface Treatment for Corrosion Protection of Magnesium Alloy AZ31"; Electrochem. Solid-State Lett. 2006 vol. 9, Issue 11, B52-B55/ 9(11); Abstract only; 1 page.
Galanty, et al al. "Consolidation of metal powders during the extrusion process," Journal of Materials Processing Technology (2002), pp. 491-496.
Garfield, "Formation Damage Control Utilizing Composite-Bridge-Plug Technology for Monobore, Multizone Stimulation Operations," SPE 70004, 2001, Society of Petroleum Engineers Inc., This paper was prepared for presentation at the SPE Per.
Garfield, et al., "Maximizing Inflow Performance in Soft Sand Completions Using New One-trip Sand Control Liner Completion Technology", SPE European Formation Damage Conference, May 25-27, 2005.
Goh, et al., "Development of novel carbon nanotube reinforced magnesium nanocomposites using the powder metallurgy technique", Nanottechnology 17 (2006) 7-12.
Han, et al., "Mechanical Properties of Nanostructured Materials", Rev. Adv. Mater. Sci. 9(2005) 1-16.
Hermawan, et al., "Iron-manganese: new class of metallic degradable biomaterials prepared by powder metallurgy", Powder Metallurgy, vol. 51, No. 1, (2008), pp. 38-45.
Hjortstam, et al. "Can we achieve ultra-low resistivity in carbon nanotube-based metal composites," Applied Physics A (2004), vol. 78, Issue 8, pp. 1175-1179.
Hsiao, et al., "Baking Treatment Effect on Materials Characteristics and Electrochemical Behavior of anodic Film Formed on AZ91D Magnesium Alloy"; Corrosion Science; 49; pp. 781-793; (2007).
Hsiao, et al., "Effect of Heat Treatment on Anodization and Electrochemical Behavior of AZ91D Magnesium Alloy"; J. Mater. Res.; 20(10); pp. 2763-2771;(2005).
International Search Report and Written Opinion; International Application No. PCT/US2010/057763; International Filing Date: Nov. 23, 2010; Dated: Jul. 28, 2011; 10 pages.
International Search Report and Written Opinion; International Application No. PCT/US2010/059257; International Filing Date: Dec. 7, 2010; Dated: Jul. 27, 2011; 8 pages.
International Search Report and Written Opinion; International Application No. PCT/US2010/059259; International Filing Date: Dec. 7, 2010; Dated: Jun. 13, 2011; 8 pages.
International Search Report and Written Opinion; International Application No. PCT/US2010/059263; International Filing Date: Dec. 7, 2010; Dated: Jul. 8, 2011; 9 pages.
International Search Report and Written Opinion; International Application No. PCT/US2010/059265; International Filing Date: Dec. 7, 2010; Dated: Jun. 16, 2011; 8 pages.

(56) References Cited

OTHER PUBLICATIONS

International Search Report and Written Opinion; International Application No. PCT/US2010/059268; International Filing Date: Dec. 7, 2010; Dated: Jun. 17, 2011; 8 pages.
International Search Report and Written Opinion; International Application No. PCT/US2011/043036; International Filing Date: Jul. 6, 2011; Dated: Feb. 23, 2012; 9 pages.
International Search Report and Written Opinion; International Application No. PCT/US2011/047000; International Filing Date: Aug. 9, 2011; Dated: Dec. 26, 2011; 8 pages.
International Search Report and Written Opinion; International Application No. PCT/US2011/058099; International Filing Date: Oct. 27, 2011; Dated: May 11, 2012; 12 pages.
International Search Report and Written Opinion; International Application No. PCT/US2012/046231; International Filing Date: Jul. 11, 2012; Dated: Jan. 29, 2013; 9 pages.
International Search Report and Written Opinion; International Application No. PCT/US2012/049434; International Filing Date: Aug. 3, 2012; Dated: Feb. 1, 2013; 7 pages.
International Search Report and Written Opinion; International Application No. PCT/US2012/053339; International Filing Date: Aug. 31, 2012; Dated: Feb. 15, 2013; 11 pages.
International Search Report and Written Opinion; International Application No. PCT/US2012/053342; International Filing Date: Aug. 31, 2012; Dated: Feb. 19, 2013; 9 pages.
International Search Report and Written Opinion; International Application No. PCT/US2012/053350; International Filing Date: Aug. 31, 2012; Dated: Feb. 25, 2013; 10 pages.
International Search Report and Written Opinion; International Application No. PCT/US2012/071742; International Filing Date: Dec. 27, 2012; Dated: Apr. 22, 2013; 12 pages.
Lavernia, et al.,"Cryomilled Nanostructured Materials: Processing and Properties", Materials Science and Engineering A, 493, (2008) pp. 207-214.
Li, "Design of Abrasive Water Jet Perforation and Hydraulic Fracturing Tool," Oil Field Equipment, Mar. 2011.
Maisano, "Cryomilling of Aluminum-Based and Magnesium-Based Metal Powders", Thesis, Virginia Tech, Jan. 13, 2006.
Seyni, et al., "On the interest of using degradable fillers in co-ground composite materials", Powder Technology 190, (2009) pp. 176-184.
Vahlas, et al., "Principles and Applications of CVD Powder Technology", Materials Science and Engineering R 53 (2006) pp. 1-72.
"Baker Hughes Refines Expandable Tubular Technology with Abaqus and Isight", Simulia Realistic Simulation News, Jan./Feb. 2011, pp. 12-13.
"Reactivity series", Wikipedia, http://en.wikipedia.org/w/index.php?title=Reactivity_series&printable=yes downloaded on May 18, 2014. 8 pages.
Bakshi et al., "Carbon nanotube reinforced metal matrix composites—a review," International Materials Reviews; 2010, pp. 41-64, vol. 55, No. 1.
Birbilis, et al., "Exploring Corrosion Protection of Mg Via Ionic Liquid Pretreatment", Surface & Coatings Technology; 201, pp. 4496-4504, (2007).
Canadian Office Action for Canadian Application No. 2,833,958, dated Sep. 23, 2014, pp. 1-2.
Chinese Office Action for Chinese Application No. 201080055613.5, dated Nov. 4, 2014, pp. 1-20.
Chinese Office Action for Chinese Application No. 201180012447.5, dated Jul. 3, 2014, 7 pages.
Chinese Office Action for Chinese Application No. 201180052095.6, dated Jul. 21, 2014, pp. 1-32.
Feng, et al., "Electroless Plating of Carbon Nanotubes with Silver" Journal of Materials Science, 39, (2004) pp. 3241-3243.
International Search Report and Written Opinion; International Application No. PCT/US2012/038622; International Filing Date: May 18, 2012; Dated: Dec. 6, 2012; 12 pages.
International Search Report and Written Opinion; International Application No. PCT/US2013/020046; International Filing Date: Jan. 3, 2013; Dated: Apr. 10, 2013; 7 pages.
International Search Report and Written Opinion; International Application No. PCT/US2014/054720; International Filing Date: Sep. 9, 2014; Dated: Dec. 17, 2014; 10 pages.
International Search Report for related PCT Application No. PCT/US2013/035258, dated Jul. 4, 2013, pp. 1-4.
International Search Report for related PCT Application No. PCT/US2013/035261, dated Jul. 10, 2013, pp. 1-4.
International Search Report for related PCT Application No. PCT/US2013/035262, dated Jul. 1, 2013, pp. 1-4.
International Search Report for related PCT Application No. PCT/US2013/068062, dated Feb. 12, 2014, pp. 1-3.
Lee, et al., "Effects of Ni addition on hydrogen storage properties of Mg17AL12 alloy", Materials Chemistry and Physics, 2011, 126, pp. 319-324.
Li, et al., "Investigation of aluminium-based nancompsoites with ultra-high strength", Materials Science and Engineering A, 527, pp. 305-316, (2009).
Liu, et al.; "Electroless Nickel Plating on AZ91 Mg Alloy Substrate"; Surface & Coatings Technology; 200; pp. 5087-5093; (2006).
Mathis, "Sand Management: A Review of Approaches and Concerns", Society of Petroleum Engineers, SPE Paper No. 82240, SPE European Formation Damage Conference, The Hague, The Netherlands, May 13-14, 2003.
Pardo, et al.; "Corrosion Behaviour of Magnesium/Aluminium Alloys in 3.5 wt% NaC1"; Corrosion Science; 50; pp. 823-834; (2008).
Quik Drill Composite Frac Plug; Baker Hughes, Baker Oil Tools; Copyright 2002; 3 pages.
Shi, et al.; "Influence of the Beta Phase on the Corrosion Performance of Anodised Coatings on Magnesium-Aluminium Alloys"; Corrosion Science; 47; pp. 2760-2777; (2005).
Shimizu, et al.; "Multi-walled carbon nanotube-reinforced magnesium alloy composites", Scripta Materialia, vol. 58, Issue 4, Feb. 2008, pp. 267-270.
Shumbera, et al. "Improved Water Injector Performance in a Gulf of Mexico Deepwater Development Using an Openhole Frac Pack Completion and Downhole Filter System: Case History." SPE Annual Technical Conference and Exhibition, Oct. 5-8, 2003.
Song, et al.; "Corrosion Mechanisms of Magnesium Alloys"; Advanced Engineering Materials; 1(1); pp. 11-33; (1999).
Song, et al.; "Influence of Microstructure on the Corrosion of Diecast AZ91D"; Corrosion Science; 41; pp. 249-273; (1999).
Song, et al.; "Understanding Magnesium Corrosion"; Advanced Engineering Materials; 5; No. 12; pp. 837-858; (2003).
Sun, et al.; "Colloidal Processing of Carbon Nanotube/Alumina Composites" Chem. Mater. 2002, 14, pp. 5169-5172.
Vickery, et al.; "New One-Trip Multi-Zone Frac Pack System with Positive Positioning." European Petroleum Conference, Oct. 29-31, 2002, Aberdeen, UK. [Abstract Only].
Zeng, et al. "Progress and Challenge for Magnesium Alloys as Biomaterials," Advanced Engineering Materials, vol. 10, Issue 8, Aug. 2008, pp. B3-B14.
Zhang, et al.; "High Strength Nanostructured Materials and Their Oil Field Applications"; Society of Petroleum Engineers; Conference Paper SPE 157092; SPE International Oilfield Nanotechnology Conference, 2012; 6 pages.
Zhang, et al.; "Metal Coating on Suspended Carbon Nanotubes and its Implication to Metal—Tube Interaction", Chemical Physics Letters 331 (2000) 35-41.
Adams, et al.; "Thermal stabilities of aromatic acids as geothermal tracers", Geothermics, vol. 21, No. 3, 1992, pp. 323-339.
Aviles et al, "Degradable Alternative to Risky Mill-Out Operations in Plug and PERF"; SPE-173695-MS; Society of Petroleum Engineers; SPE/ICOTA Coiled Tubing & Well Intervention Conference & Exhibition; Mar. 24-25, 2015; 10 Pages.
Ayman, et al.; "Effect of Consolidation and Extrusion Temperatures on Tensile Properties of Hot Extruded ZK61 Magnesium Alloy Gas Atomized Powders via Spark Plasma Sintering", Transactions of JWRI, vol. 38 (2009), No. 2, pp. 1-5.

(56) References Cited

OTHER PUBLICATIONS

Baker Hughes Incorporated. IN-Tallic Disintegrating Frac Balls. Houston: Baker Hughes Incorporated, 2011. Accessed Mar. 6, 2015.
Baker Hughes, "Multistage", Oct. 31, 2011, BakerHughes.com; accessed Mar. 6, 2015.
Bin et al., "Advances in Fluidization CVD Technology", East China University of Chemical Technology, China Academic Journal Electronic Publishing House, vol. 13, No. 4, Nov. 1992, pp. 360-365, English Abstract on p. 366.
Canadian Office Action for Canadian Application No. 2,833,981, dated Sep. 23, 2014, pp. 1-2.
Canadian Office Action for Canadian Application No. 2,834,794, dated Dec. 15, 2014, pp. 1-3.
Canadian Office Action for Canadian Application No. 2,841,068, dated Jan. 23, 2015, pp. 1-3.
Canadian Office Action for Canadian Application No. 2,841,078, dated Oct. 7, 2014, pp. 1-2.
Canadian Office Action for Canadian Application No. 2,841,132, dated Mar. 11, 2015, pp. 1-4.
Canadian Office Action for Canadian Application No. 2,841,184, dated Apr. 16, 2015, pp. 1-5.
Canadian Office Action for Canadian Application No. 2,842,962, dated Mar. 19, 2015, pp. 1-6.
Canadian Office Action for Canadian Application No. 2,843,011, dated Mar. 31, 2015, pp. 1-4.
Canadian Office Action for Canadian Application No. 2,844,517, dated May 26, 2015, pp. 1-4.
Canadian Office Action for Canadian Application No. 2,845,339, dated May 1, 2015, pp. 1-1.
Canadian Office Action for Canadian Application No. 2,860,699, dated Jul. 16, 2015, pp. 1-4.
Chinese Office Action; Chinese Application No. 201180052095.6; Dated: Mar. 18, 2015; pp. 1-19.
Chinese Office Action; Chinese Application No. 201280036253.3; Dated: Apr. 22, 2015; 21 pages.
Chinese Office Action; Chinese Application No. 201280036260.3; Dated: May 27, 2015; pp. 1-18.
Danish Search Report and Opinion for Danish Application No. PA 2013 00060, dated Dec. 12, 2014, pp. 1-6.
International Search Report and Written Opinion; International Application No. PCT/US2012/047163; International Filing Date: Jul. 18, 2012; Dated Feb. 26, 2013; 12 pages.
International Search Report and Written Opinion; International Application No. PCT/US2012/052836; International Filing Date: Aug. 29, 2012; Dated Feb. 1, 2013; 9 pages.
International Search Report and Written Opinion; International Application No. PCT/US2013/050475; International Filing Date: Jul. 15, 2013; Dated: Oct. 10, 2013; 12 pages.
International Search Report and Written Opinion; International Application No. PCT/US2014/058997, International Filing Date: Oct. 3, 2014; Dated: Jan. 12, 2015; 12 pages.
Lin et al., "Processing and Microstructure of Nano-Mo/Al2O3 Composites from MOCVD and Fluidized Bed", Nanostructured Materials, Nov. 1999, vol. 11, No. 8, pp. 1361-1377.
Rose, et al.; "The application of the polyaromatic sulfonates as tracers in geothermal reservoirs", Geothermics 30 (2001) pp. 617-640.
Shigematsu, et al., "Surface Treatment of AZ91D Magnesium Alloy by Aluminum diffusion Coating", Journal of Materials Science Letters 19, 2000, pp. 473-475.
Singh, et al., "Extended Homogeneity Range of Intermetallic Phases in Mechanically Alloyed Mg—Al Alloys", Elsevier Sciences Ltd., Intemetallics 11, 2003, pp. 373-376.
Spencer et al., "Fluidized Bed Polymer Particle ALD Process for Producing HDPE/Alumina Nanocomposites", The 12th International Conference on Fluidization—New Horizons in Fluidization Engineering, vol. RP4 (2007).
Stanley, et al.; "An Introduction to Ground-Water Tracers", Department of Hydrology and Water Resources, University of Arizona, Mar. 1985, pp. 1-219.

Zemel, "Tracers in the Oil Field", University of Texas at Austin, Center for Petroleum and Geosystems, Jan. 1995, Chapters 1, 2, 3, 7.
"Declaration of Karl T. Hartwig in Support of Petitioner Pursuant to 37 C.F.R. § 42.120", dated Nov. 21, 2016 in support of U.S. Pat. No. 8,573,295, 52 pages.
Petition for Inter Partes Review; Case No. IPR2017-00326; U.S. Pat. No. 9,101,978; dated Nov. 23, 2016; 46 pages.
Petition for Inter Partes Review; Case No. IPR2017-00327; U.S. Pat. No. 8,573,295; dated Nov. 23, 2016; 53 pages.
"Optisleeve Sliding Sleeve", [online]; [retrieved on Jun. 25, 2010]; retrieved from the Internet weatherford.com/weatherford/groups/ . . . /weatherfordcorp/WFT033159.pdf.
Baker Hughes, "Flow Control Systems," [online]; [retrieved on May 20, 2010]; retrieved from the Internet http://www.bakerhughes.com/products-and-services/completions-and-productions/well-completions/packers-and-flow-control/flow-control-systems.
Bououdina, et al., "Comparative Study of Mechanical Alloying of (Mg+Al) and (Mg+Al+Ni) Mixtures for Hydrogen Storage", J. Alloys, Compds, 2002, 336, 222-231.
Canadian Office Action for Canadian Application No. 2,783,241, dated Feb. 25, 2013, pp. 1-3.
Canadian Office Action for Canadian Application No. 2,783,346, dated Feb. 21, 2013, pp. 1-4.
Carrejo, et al., "Improving Flow Assurance in Multi-Zone Fracturing Treatments in Hydrocarbon Reservoirs with High Strength Corrodible Tripping Balls"; Society of Petroleum Engineers; SPE Paper No. 151613; Apr. 16, 2012; 5 pages.
Coronado, "Development of an Internal Coiled Tubing Connector Utilizing Permanent Packer Technology"; Society of Petroleum Engineers, SPE Paper No. 46036; Apr. 15, 1998; 10 pages.
Garfield, New One-Trip Sand-Control Completion System that Eliminates Formation Damage Resulting From conventional Perforating and Gravel-Packing Operations:, SPE Annual Technical Conference and Exhibition, Oct. 9-12, 2005.
Gray, et al., "Protective Coatings on Magnesium and Its Alloys—a Critical Review", Journal of Alloys and Compounds 336 (2002), pp. 88-113.
Hsiao, et al., "Anodization of AZ91D Magnesium Alloy in Silicate-Containing Electrolytes"; Surface & Coatings Technology; 199; pp. 127-134; (2005).
Hsiao, et al., "Characterization of Anodic Films Formed on AZ91D Magnesium Alloy"; Surface & Coatings Technology; 190; pp. 299-308; (2005).
Huo et al.; "Corrosion of AZ91D Magnesium Alloy with a Chemical Conversion Coating and Electroless Nickel Layer"; Corrosion Science: 46; pp. 1467-1477; (2004).
International Search Report and Written Opinion; International Application No. PCT/US2011/058105; International Filing Date: Oct. 27, 2011; Dated: May 1, 2012; 8 pages.
International Search Report and Written Opinion; International Application No. PCT/US2012/034973; International Filing Date: Apr. 25, 2012; Dated: Nov. 29, 2012; 8 pages.
International Search Report and Written Opinion; International Application No. PCT/US2012/034978; International Filing Date: Apr. 25, 2012; Dated: Nov. 12, 2012; 9 pages.
International Search Report and Written Opinion; International Application No. PCT/US2012/044866; International Filing Date: Jun. 29, 2012; Dated: Jan. 2, 2013; 9 pages.
International Search Report and Written Opinion; International Application No. PCT/US2014/010862; International Filing Date: Jan. 9, 2014; Dated: Apr. 21, 2014; 9 pages.
International Search Report; International Application No. PCT/US2012/044229, International Filing Date: Jun. 26, 2012; Dated; Jan. 30, 2013; 3 pages.
Kuzumaki, et al.; "Mechanical Characteristics and Preparation of Carbon Nanotube Fiber-Reinforced Ti Composite", Advanced Engineering Materials, 2000, 2, No. 7.
Liu, et al., "Calculated Phase Diagrams and the Corrosion of Die-Cast Mg—Al Alloys", Corrosion Science, 2009, 51, 606-619.
Lunder et al.; "The Role of Mg17Al12 Phase in the Corrosion of Mg Alloy AZ91"; Corrosion; 45(9); pp. 741-748; (1989).

(56) References Cited

OTHER PUBLICATIONS

Majumdar, et al., "Laser Surface Engineering of a Magnesium Alloy with Al + Al2O3", Surface and Coatings Technology 179 (2004) pp. 297-305.

Murray, "Binary Alloy Phase Diagrams" Int. Met. Rev., 30(5) 1985 vol. 1, pp. 103-187.

Nie, "Patents of Methods to Prepare Intermetallic Matrix Composites: A Review", Recent Patents on Materials Science 2008, vol. 1, pp. 232-240.

Saravanan et al., "Mechanically Alloyed Carbon Nanotubes (CNT) Reinforced Nanocrystalline AA 4032: Synthesis and Characterization," Journal of Minerals & Materials Characterization & Engineering, vol. 9, No. 11, pp. 1027-1035, 2010.

Shaw, "Benefits and Application of a Surface-Controlled Sliding Sleeve for Fracturing Operations"; Society of Petroleum Engineers, SPE Paper No. 147546; Oct. 30, 2011; 8 pages.

Song, "Recent Progress in Corrosion and Protection of Magnesium Alloys"; Advanced Engineering Materials; 7(7); pp. 563-586; (2005).

Song, et al.; "A Possible Biodegradable Magnesium Implant Material," Advanced Engineering Materials, vol. 9, Issue 4, Apr. 2007, pp. 298-302.

Song, et al.; "Corrosion Behaviour of AZ21, AZ501 and AZ91 in Sodium Chloride"; Corrosion Science; 40(10); pp. 1769-1791; (1998).

Triolo et al., "Resolving the Completion Engineer's Dilemma: Permanent or Retrievable Packer?"; Society of Petroleum Engineers, SPE Paper No. 76711; May 20, 2002; 16 pages.

Vernon Constien et al., "Development of Reactive Coatings to Protect Sand-Control Screens", SPE 112494, Copyright 2008, Society of Petroleum Engineers, Presented at the 2008 SPE International Symposium and Exhibition on Formation Damage Control.

Walters, et al.; "A Study of Jets from Unsintered-Powder Metal Lined Nonprecision Small-Caliber Shaped Charges", Army Research Laboratory, Aberdeen Proving Ground, MD 21005-5066; Feb. 2001.

Wang, et al., "Contact-Damage-Resistant Ceramic/Single-Wall Carbon Nanotubes and Ceramic/Graphite Composites" Nature Materials, vol. 3, Aug. 2004, pp. 539-544.

Watanabe, et al., "Superplastic Deformation Mechanism in Powder Metallurgy Magnesium Alloys and Composites", Acta mater. 49 (2001) pp. 2027-2037.

Watarai, Trend of research and development for magnesium alloys-reducing the weight of structural materials in motor vehicles, (2006) Science and technology trends, Quaterly review No. 18, 84-97.

Welch et al., "Nonelastomeric Sliding Sleeve Maintains Long Term Integrity in HP/HT Application: Case Histories" [Abstract Only], SPE Eastern Regional Meeting, Oct. 23-25, 1996, Columbus. Ohio.

Xu, et al., "Nanostructured Material-Based Completion Tools Enhance Well Productivity"; International Petroleum Technology Conference; Conference Paper IPTC 16538; International Petroleum Technology Conference 2013; 4 pages.

Zhan, et al., "Single-wall carbon nanotubes as attractive toughening agents in alumina-based nanocomposites" Nature Materials, vol. 2., Jan. 2003, pp. 38-42.

Zhang, et al.; "Formation of metal nanowires on suspended single-walled carbon nanotubes" Applied Physics Letter, vol. 77, No. 19 (2000), pp. 3015-3017.

Zhang, et al.; "Study on the Environmentally Friendly Anodizing of AZ91D Magnesium Alloy"; Surface and Coatings Technology: 161; pp. 36-43; (2002).

Zhu, et al., "The process of coating on ultrafine particles by surface hydrolysis reaction in a fluidized bed reactor", Surface and Coatings Technology 135 (2000) 14-17.

\* cited by examiner

HIGH TEMPERATURE TRACERS FOR DOWNHOLE DETECTION OF PRODUCED WATER

BACKGROUND

In a multi-zone oil and/or gas well, monitoring when water starts producing and the flow rate of water in each zone are important to understand the dynamics of the wellbore. Tracers have been used in the past to monitor water production in reservoirs. These tracers are typically immobilized or integrated with a polymer carrier through covalent bonds or ionic interactions. Upon contact with water, the binding between the tracers and the polymer carrier breaks thus releasing the tracers. As oil and gas production activities continue to shift toward more hostile and unconventional environments, the performance of the polymer-based tracer composites may be less than desirable as the polymer carriers are susceptible to decomposition under harsh conditions. Accordingly the industry is always receptive to new tracer composites and improved methods for monitoring water production in reservoirs.

BRIEF DESCRIPTION

The above and other deficiencies in the prior art are overcome by, in an embodiment, a tracer composite comprises a tracer disposed in a metal-based carrier which comprises: a cellular nanomatrix and a metal matrix disposed in the cellular nanomatrix, wherein the tracer is detectable at a range of from about 1 ppt to about 1,000 ppm.

An article comprising the tracer composite is also disclosed.

A method of analyzing water in a fluid produced from at least one zone of a well comprises: introducing a tracer composite into the well; obtaining a sample of the fluid produced from at least one zone of the well; and analyzing the tracer in the sample; wherein the tracer composite comprises a tracer disposed in a metal-based carrier which comprises: a cellular nanomatrix and a metal matrix disposed in the cellular nanomatrix, wherein the tracer is detectable at a range of from about 1 ppt to about 1,000 ppm.

BRIEF DESCRIPTION OF THE DRAWINGS

The following descriptions should not be considered limiting in any way. With reference to the accompanying drawings, like elements are numbered alike.

DETAILED DESCRIPTION

Figure 1:
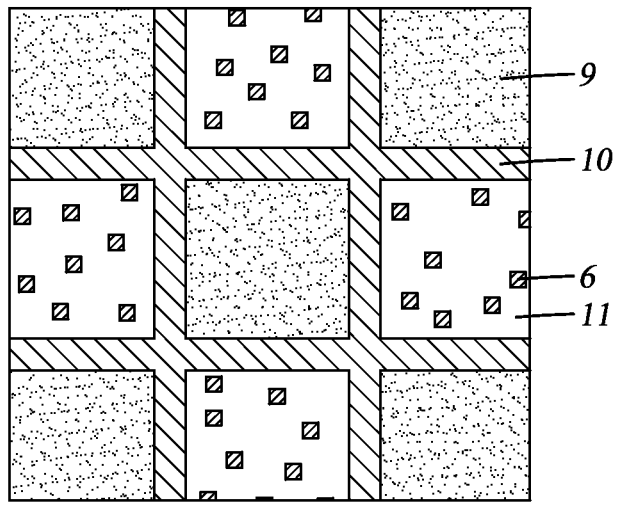
FIG. 1 illustrates a tracer composite according to an embodiment of the disclosure.

The inventors hereof have found that the temperature rating of tracer composites can be greatly improved by incorporating tracers into disintegrable metal-based carriers. The metal-based carriers are stable in the presence of hydrocarbons but can controllably dissolve in the presence of water. Accordingly, when the tracer composites are in contact with produced water, the metal-based carriers dissolve at a controlled rate releasing the tracers as a function of the concentration of water and the environmental temperature. Compared with polymer-based carriers, metal-based carriers are much more stable thus can significantly enhance the temperature rating of the tracer composites. For example, while commercially available polymer-based tracer composites typically have a temperature rating of about 350° F., the tracer composites of the disclosure can be used at a temperature of up to about 650° F. In addition, when the service function of the tracer composites is complete, the metal-based carriers can completely dissolve without interfering with fluid production or other downhole operations.

Advantageously, the tracers are stable at temperatures up to about 650° F., up to about 600° F., up to about 550° F. or up to about 500° F. depending on the application and the specific tracers used. As a further advantageous feature, the tracers can be detected with sensitivity up to the order of part-per-trillion (ppt). In an embodiment, the tracer is detectable at a range of from about 1 ppt to about 1,000 ppm, about 5 ppt to about 1,000 ppm, or about 50 ppt to about 500 ppm. The tracers in the tracer composites comprise one or more of the following: inorganic cations and/or inorganic anions; stable isotopes; activable elements/isotopes; or organic compounds.

The exemplary inorganic cations (also referred to as "characteristic cations") include the cations of metals such as thorium, silver, bismuth, zirconium, chromium, copper, beryllium, cadmium, manganese, tin, rare earth metals, nickel, iron, cobalt, zinc, gallium, and the like. As used herein, rare earth metals include scandium, yttrium, lanthanum, cerium, praseodymium, neodymium, promethium, samarium, europium, gadolinium, terbium, dysprosium, holmium, eribium, thulium, ytterbium, or lutetium. In an embodiment, the metals of the characteristic cations are distinct from the metals that may be present in the formation so that it is clear that the detected characteristic cations are from the tracer composites instead of the formation.

Suitable inorganic anions (also referred to as "characteristic anions") include complex cyanides such as dicyanoaurate complex ion $Au(CN)_2^-$, tetracyanoickelate $Ni(CN)_4^{2-}$, $Co(CN)_6^{3-}$, $Fe(CN)_6^{3-}$, nitrate, iodide and thiocyanate.

The characteristic anions and characteristic cations can be used independently. For example, the anions can be used in the form of salts like sodium salts and potassium salts where the corresponding cations are not characteristic cations. Alternatively, the characteristic anions and characteristic cations can be used together as the tracer materials. Liquid chromatography and ion chromatography may be applied to elute the tracers and to improve the detectability of the tracers.

Stable isotopes in nitrates, ammonium salts, sulfates, carbonates can also provide a unique signature. Exemplary isotopes include isotopes of oxygen ($^{16}O$, $^{18}O$), isotopes of nitrogen ($^{14}N$, $^{15}N$), sulfur isotopes ($^{32}S$, $^{34}S$, $^{36}S$), carbon isotopes ($^{12}C$, $^{13}C$), strontium isotopes ($^{86}Sr$, $^{87}Sr$), hydrogen isotopes ($^{1}H$, $^{2}H$), boron isotopes ($^{10}B$, $^{11}B$), or chlorine isotopes ($^{35}Cl$, $^{37}Cl$).

The tracers can include activable tracers, which are non-radioactive but can be activated by neutron radiation when needed, forming new gamma-emitting tracers. Advantageously, these tracers have a very short half-life or decay very quickly. For example, the tracers can have a half-life less than about 30 days, less than about 15 days, less than about 2 days, or less than about 1 day. The activatable tracers can be diluted to reduce their level when activated. Suitable tracers include $^{69}$Ga(n, 2n)$^{68}$Ga, $^{121}$Sb(n, 2n)$^{120}$Sb, $^{138}$Ba(n, 2n)$^{137m}$Ba, $^{63}$Cu(n, 2n)$^{62}$Cu. Other activatable tracers having a short half-life can also be used. The activable tracers can be activated right before sampling. For example, by selectively activating an activable tracer downhole in a particular zone or location, the information of water produced from that particular zone or location can be obtained. In this embodiment, the tracers for different zones can be the same. Alternatively, the tracer can be activated after a sample has been collected and before or when the sample is analyzed in a downstream location, for example on the ground. In this embodiment, the tracers for different zones can be different.

The tracers also include organic compounds. Certain aromatic acids and compounds can be separated and detected with high sensitivity (ppb) by ion chromatography and UV detection with significant aromatic character. Exemplary organic tracer compounds include pentafluorobenzoate; meta-trifluoromethylbenzoate; tetrafluorophthalate; 2,3-difluorobenzoic acid; 2,3-dimethylbenzoic acid; 2,4,6-trimethylbenzoic acid; 2,4-difluorobenzoic acid; 2,4-difluorophenylacetic acid; 2,4-dimethylbenzoic acid; 2,5-dimethylbenzoic acid; 2,5-dimethylbenzenesulfonic acid; 2,6-difluorobenzoic acid; 2,6-difluorophenylacetic acid; 2,6-dimethylbenzoic acid; 3,4-difluorobenzoic acid; 3,4-dimethylbenzoic acid; 3,5-dimethylbenzoic acid; 3,5-di(trifluoromethyl)benzoic acid; 3,5-di(trifluoromethyl)phenylacetic acid; 3-fluoro-4-methylbenzoic acid; 4-ethylbenzenesulfonic acid; 4-ethylbenzenesulfonic acid; 4-methylbenzenesulfonic acid; benzoic acid; benzenesulfonic acid; isophthalic acid; meta-fluorobenzoic acid; meta-fluorophenylacetic acid; meta-trifluoromethylbenzoic acid; meta-trifluoromethylphenylacetic acid; ortho-fluorobenzoic acid; ortho-trifluorophenylacetic acid; ortho-trifluoromethylbenzoic acid; ortho-trifluoromethylphenylacetic acid; phthalic acid; perfluorobenzoic acid; perfluorobenzenesulfonic acid; perfluorophenylacetic acid; para-fluorobenzoic acid; para-fluorophenylacetic acid; para-trifluoromethylbenzoic acid; para-trifluoromethylphenylacetic acid; or terephthalic acid.

Polyaromatic sulfonates have outstanding thermal stability and are stable at temperatures of up to about 650° F. or up to about 570° F. Exemplary sulfonates include 1,3,6,8-pyrene tetrasulfonate, 1,5-naphthalene disulfonate, 1,3,6-naphthalene trisulfonate, 2-naphthalene sulfonate, and 2,7-naphthalene disulfonate. Polyaromatic sulfonates can exhibit fluorescence. Their detectable concentration is in the parts per trillion (ppt) range by high performance liquid chromatography and fluorescence spectroscopy techniques.

The metal-based carriers in the tracer composites are metal composites including a cellular nanomatrix and a metal matrix disposed in the cellular nanomatrix. The cellular nanomatrix comprises a nanomatrix material. The metal matrix (e.g. a plurality of particles) comprises a particle core material dispersed in the cellular nanomatrix. The particle core material comprises a nanostructured material. Such a metal composite having the cellular nanomatrix with metal matrix disposed therein is referred to as controlled electrolytic metallic. An exemplary metal composite and method used to make the metal composite are disclosed in U.S. patent application Ser. Nos. 12/633,682, 12/633,688, 13/220,832, 13/220,822, and 13/358,307, the disclosure of each of which patent application is incorporated herein by reference in its entirety.

The metal matrix can include any suitable metallic particle core material that includes nanostructure as described herein. In an exemplary embodiment, the metal matrix is formed from particle cores and can include an element such as aluminum, iron, magnesium, manganese, zinc, or a combination thereof, as the nanostructured particle core material. More particularly, in an exemplary embodiment, the metal matrix and particle core material can include various Al or Mg alloys as the nanostructured particle core material, including various precipitation hardenable alloys Al or Mg alloys. More than one alloy can be present in the metal matrix. For example, the metal matrix comprises a plurality of particles wherein some of the particles are Al alloys and others are Mg alloys. In some embodiments, the particle core material includes magnesium and aluminum where the aluminum is present in an amount of about 1 weight percent (wt %) to about 15 wt %, specifically about 1 wt % to about 10 wt %, and more specifically about 1 wt % to about 5 wt %, based on the weight of the metal matrix, the balance of the weight being magnesium.

In an additional embodiment, precipitation hardenable Al or Mg alloys are particularly useful because they can strengthen the metal matrix through both nanostructuring and precipitation hardening through the incorporation of particle precipitates as described herein. The metal matrix and particle core material also can include a rare earth element, or a combination of rare earth elements. Exemplary rare earth elements include Sc, Y, La, Ce, Pr, Nd, or Er. A combination comprising at least one of the foregoing rare earth elements can be used. Where present, the rare earth element can be present in an amount of about 5 wt % or less, and specifically about 2 wt % or less, based on the weight of the metal composite.

The metal matrix and particle core material also can include a nanostructured material. In an exemplary embodiment, the nanostructured material is a material having a grain size (e.g., a subgrain or crystallite size) that is less than about 200 nanometers (nm), specifically about 10 nm to about 200 nm, and more specifically an average grain size less than about 100 nm. It will be appreciated that the nanocellular matrix and grain structure of the metal matrix are distinct features of the metal composite. Particularly, nanocellular matrix is not part of a crystalline or amorphous portion of the metal matrix.

The cellular matrix includes aluminum, cobalt, copper, iron, magnesium, nickel, silicon, tungsten, zinc, an oxide thereof, a nitride thereof, a carbide thereof, an intermetallic compound thereof, a cermet thereof, or a combination comprising at least one of the foregoing.

The metal matrix can be present in an amount from about 50 wt % to about 95 wt %, specifically about 60 wt % to about 95 wt %, and more specifically about 70 wt % to about 95 wt %, based on the weight of the metal composite. Further, the amount of the metal nanomatrix material is about 10 wt % to about 50 wt %, specifically about 20 wt % to about 50 wt %, and more specifically about 30 wt % to about 50 wt %, based on the weight of the metal composite.

The metal composite can include a disintegration agent to control the disintegration rate of the metal composite. The disintegration agent can be disposed in the metal matrix, the cellular nanomatrix, or a combination thereof. According to an embodiment, the disintegration agent includes a metal, fatty acid, ceramic particle, or a combination comprising at least one of the foregoing, the disintegration agent being disposed among the controlled electrolytic material to change the disintegration rate of the controlled electrolytic material. In one embodiment, the disintegration agent is disposed in the cellular nanomatrix external to the metal matrix. In a non-limiting embodiment, the disintegration agent increases the disintegration rate of the metal composite. In another embodiment, the disintegration agent decreases the disintegration rate of the metal composite. The disintegration agent can be a metal including cobalt, copper, iron, nickel, tungsten, zinc, or a combination comprising at least one of the foregoing. In a further embodiment, the disintegration agent is the fatty acid, e.g., fatty acids having 6 to 40 carbon atoms. Exemplary fatty acids include oleic acid, stearic acid, lauric acid, hyroxystearic acid, behenic acid, arachidonic acid, linoleic acid, linolenic acid, recinoleic acid, palmitic acid, montanic acid, or a combination comprising at least one of the foregoing. In yet another embodiment, the disintegration agent is ceramic particles such as boron nitride, tungsten carbide, tantalum carbide, titanium carbide, niobium carbide, zirconium carbide, boron carbide, hafnium carbide, silicon carbide, niobium boron carbide, aluminum nitride, titanium nitride, zirconium nitride, tantalum nitride, or a combination comprising at least one of the foregoing. Additionally, the ceramic particle can be one of the ceramic materials discussed below with regard to the strengthening agent. Such ceramic particles have a size of 5 µm or less, specifically 2 µm or less, and more specifically 1 µm or less. The disintegration agent can be present in an amount effective to cause disintegration of the metal composite 200 at a desired disintegration rate, specifically about 0.25 wt % to about 15 wt %, specifically about 0.25 wt % to about 10 wt %, specifically about 0.25 wt % to about 1 wt %, based on the weight of the metal composite.

In metal composite, the metal matrix dispersed throughout the cellular nanomatrix can have an equiaxed structure in a substantially continuous cellular nanomatrix or can be substantially elongated along an axis so that individual particles of the metal matrix are oblately or prolately shaped, for example. In the case where the metal matrix has substantially elongated particles, the metal matrix and the cellular nanomatrix may be continuous or discontinuous. The size of the particles that make up the metal matrix can be from about 50 nm to about 800 µm, specifically about 500 nm to about 600 µm, and more specifically about 1 µm to about 500 µm. The particle size of can be monodisperse or polydisperse, and the particle size distribution can be unimodal or bimodal. Size here refers to the largest linear dimension of a particle.

In an embodiment, the metal composite has a metal matrix that includes particles having a particle core material. Additionally, each particle of the metal matrix is disposed in a cellular nanomatrix which is a network that substantially surrounds the component particles of the metal matrix.

As used herein, the term cellular nanomatrix does not connote the major constituent of the powder compact, but rather refers to the minority constituent or constituents, whether by weight or by volume. This is distinguished from most matrix composite materials where the matrix comprises the majority constituent by weight or volume. The use of the term substantially continuous, cellular nanomatrix is intended to describe the extensive, regular, continuous and interconnected nature of the distribution of nanomatrix material within the metal composite. As used herein, "substantially continuous" describes the extension of the nanomatrix material throughout the metal composite such that it extends between and envelopes substantially all of the metal matrix. Substantially continuous is used to indicate that complete continuity and regular order of the cellular nanomatrix around individual particles of the metal matrix are not required. For example, defects in the coating layer over particle core on some powder particles may cause bridging of the particle cores during sintering of the metal composite, thereby causing localized discontinuities to result within the cellular nanomatrix, even though in the other portions of the powder compact the cellular nanomatrix is substantially continuous and exhibits the structure described herein. In contrast, in the case of substantially elongated particles of the metal matrix (i.e., non-equiaxed shapes), such as those formed by extrusion, "substantially discontinuous" is used to indicate that incomplete continuity and disruption (e.g., cracking or separation) of the nanomatrix around each particle of the metal matrix, such as may occur in a predetermined extrusion direction. As used herein, "cellular" is used to indicate that the nanomatrix defines a network of generally repeating, interconnected, compartments or cells of nanomatrix material that encompass and also interconnect the metal matrix. As used herein, "nanomatrix" is used to describe the size or scale of the matrix, particularly the thickness of the matrix between adjacent particles of the metal matrix. The metallic coating layers that are sintered together to form the nanomatrix are themselves nanoscale thickness coating layers. Since the cellular nanomatrix at most locations, other than the intersection of more than two particles of the metal matrix, generally comprises the interdiffusion and bonding of two coating layers from adjacent powder particles having nanoscale thicknesses, the cellular nanomatrix formed also has a nanoscale thickness (e.g., approximately two times the coating layer thickness as described herein) and is thus described as a nanomatrix. The thickness of the nanomatrix can be tuned during heat treatment by adjusting the temperature and the duration that the coated powder particles are heated. In an embodiment, the nanomatrix has a thickness of about 10 nm to about 200 µm, or about 1 µm to about 50 µm. Further, the use of the term metal matrix does not connote the minor constituent of metal composite, but rather refers to the majority constituent or constituents, whether by weight or by volume. The use of the term metal matrix is intended to convey the discontinuous and discrete distribution of particle core material within metal composite.

The tracers are present in an amount of about 1 to about 70 vol. %, about 2 to about 60 vol. %, or about 5 vol. to about 50 vol. % based on the total volume of the tracer composites. Traces can be uniformly dispersed in the tracer composites. The tracer can be dispersed in the metal matrix, the cellular nanomatrix, or both. As used herein, "dispersed" means that the tracer is blended with the carrier on a micrometer size level and "dispersed" does not include doping such as adding a tracer in the atomic size level where the tracer is on the lattice sites of the carrier.

In an embodiment, the tracer composites further comprise a disintegrable core. In another embodiment, the tracer composites further comprise an outer member disposed on a surface of the tracer composites. The outer member has a plurality of apertures to allow produced fluids to contact the metal-based carrier. It is appreciated that the tracer composites can include both a core and an outer member.

The core and the outer member can independently comprise one or more of the following: a disintegrable metal; a disintegrable metal alloy; or a disintegrable metal composite as disclosed herein. Exemplary materials for the tracer composite core include those consolidated or forged from coated particles having a core comprising Mg metal or an Mg alloy such as Mg—Si, Mg—Al, Mg—Zn, Mg—Mn, Mg—Al—Zn, Mg—Al—Mn, Mg—Zn—Zr, or Mg— rare earth alloys, and a coating comprising one or more of the following: Al; Ni; Fe; W; Cu; or Co. Exemplary materials for the tracer composite core also include Al, Zn, or Mn, alloyed with one or more of the following: Al; Mg; Mn; Zn; Cu; In; Ga; Si; Sn; or Pb. The materials for the outer member include those materials for the tracer composite core as well as non-degradable materials. In an embodiment, the outer member of the tracer composites comprises steel. In an embodiment, the core and the outer member have a slower disintegrating rate than the metal-based carrier (metal composite) when tested at the same testing conditions. Alternatively, the core or the outer member can be formed from materials that are not disintegrable in downhole environments.

The materials for the core and the outer member can be stronger than the material for the metal-based carrier. Thus by including a core or an outer member, the structural integrity of the tracer composites can be maintained.

Exemplary embodiments of the tracer composites are shown in FIGS. 1-4. Referring to FIG. 1, the tracer composite comprises cellular nanomatrix 10 and metal matrixes 9 and 11. The metal matrices 9 and 11 can be the same or different. In some embodiments, metal matrix 9 includes magnesium alloys, metal matrix 11 includes aluminum alloys, and the cellular nanomatrix 10 includes Ni, Fe, Cu, W, Co, and the like. Although it is shown in FIG. 1 that the tracer 6 is disposed only in metal matrix 11, it is appreciated that the tracer can be disposed in matrix 9, the cellular nanomatrix 10, or both.

Figure 2:
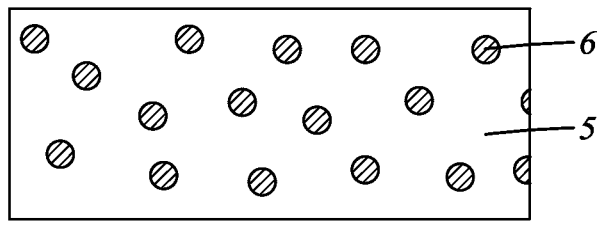
FIG. 2 illustrates a tracer composite wherein the tracer is uniformly dispersed in a metal-based carrier.
Figure 3:
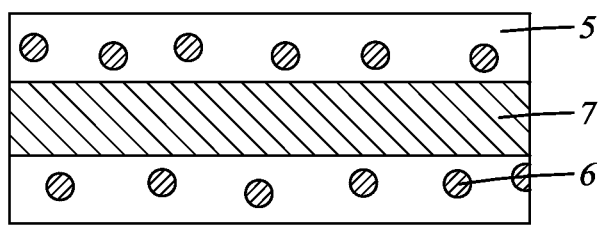
FIG. 3 illustrates an exemplary tracer composite comprising a core.
Figure 4:
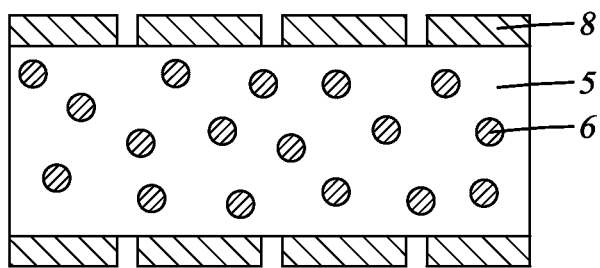
FIG. 4 illustrates an exemplary tracer composite comprising an outer member.

FIG. 2 shows that tracer 6 is uniformly distributed in a metal-based carrier 5. Referring to FIG. 3, the tracer composite further includes a disintegrable core 7. Referring to FIG. 4, the tracer composite can further include an outer member 8.

The tracer composites can be formed from a combination of, for example, tracers and powder constituents. The powder constituents include coated particles or a combination of coated particles and uncoated particles. The method includes compacting, sintering, forgoing such as by cold isostatic pressing (CIP), hot isostatic pressing (HIP), or dynamic forging. The cellular nanomatrix and nanomatrix material are formed from metallic coatings on the coated particles. The chemical composition of nanomatrix material may be different than that of coating material due to diffusion effects associated with the sintering. The metal-based carrier (metal composite) also includes a plurality of particles that make up the metal matrix that comprises the particle core material. The metal matrix and particle core material correspond to and are formed from the plurality of particle cores and core material of the plurality of powder particles as the metallic coating layers are sintered together to form the cellular nanomatrix. The chemical composition of particle core material may also be different than that of core material due to diffusion effects associated with sintering.

A method of analyzing water in a fluid produced from at least one zone of a well includes: introducing a tracer composite into the well; obtaining a sample of the fluid produced from at least one zone of the well; and analyzing the tracer in the sample.

Figure 5:
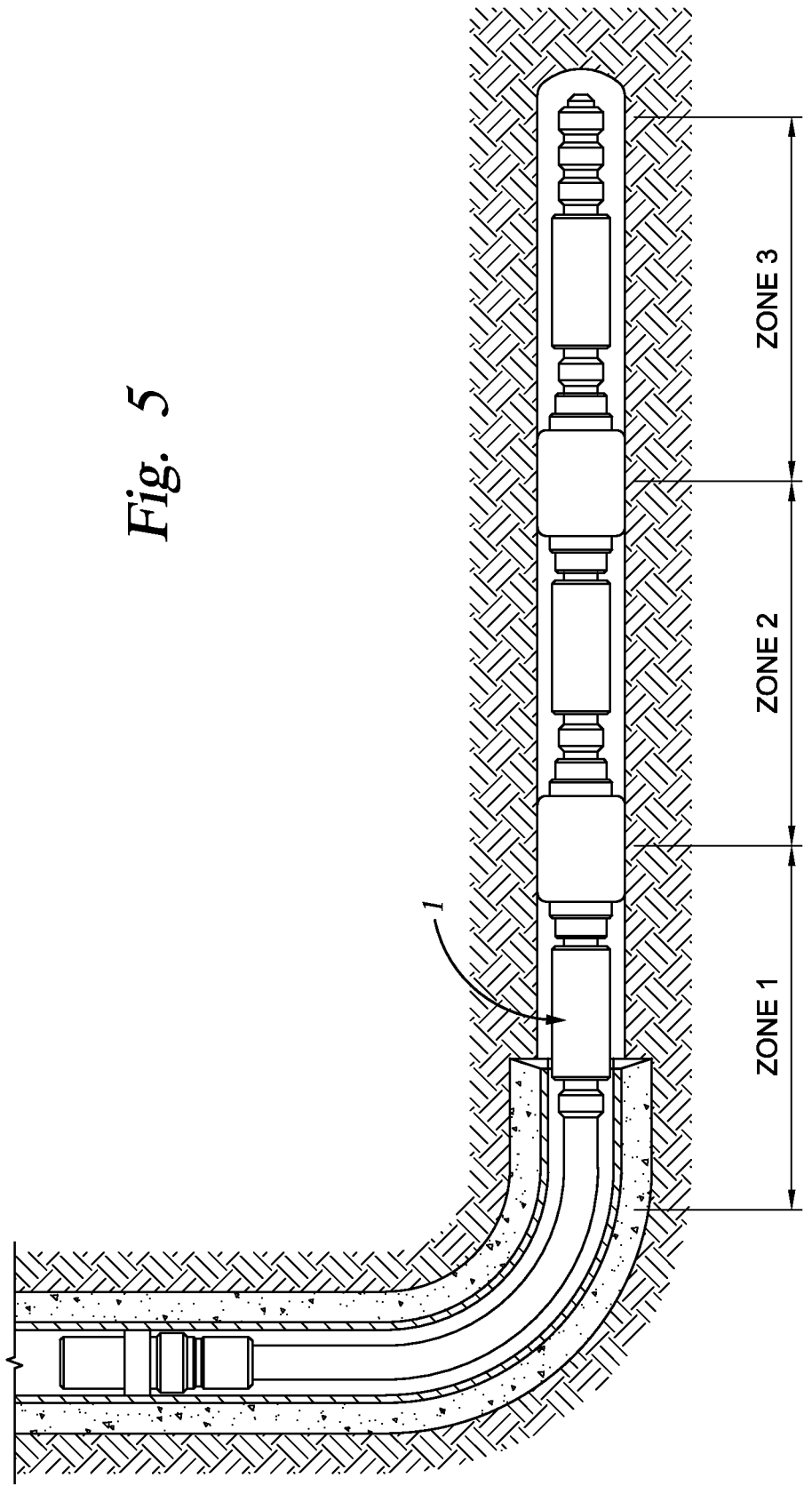
FIG. 5 illustrates a production well system for producing fluids from multiple production zones.
Figure 6:
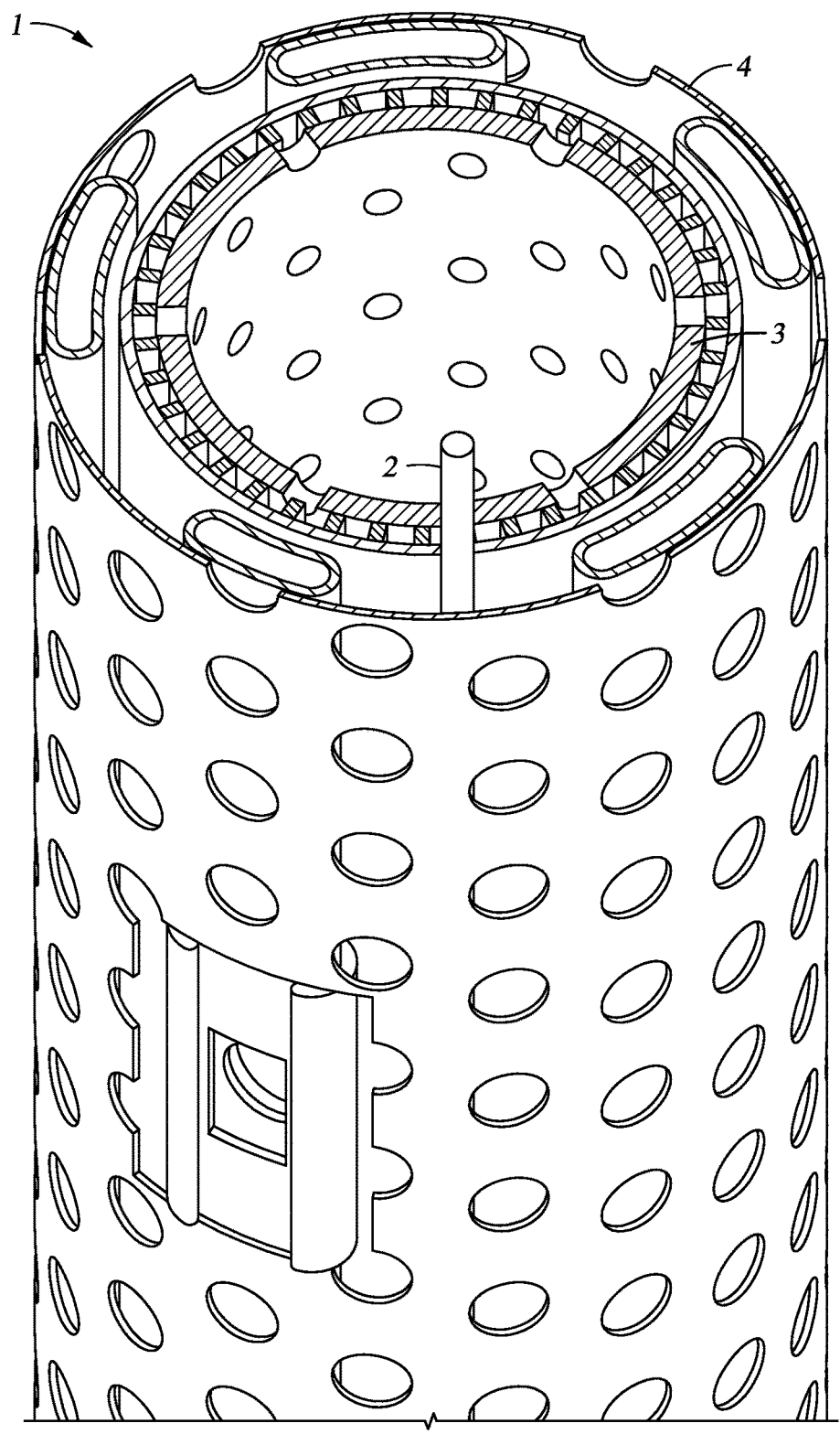
FIG. 6 is a schematic illustration of a sand screen protected by a perforated shroud used in the production well system of FIG. 5.

The tracer composites can be incorporated into various downhole articles. As an example, a metallic tracer rod 2 made of the tracer composite disclosed herein is installed between sandscreen 3 and protecting shroud 4 as shown in FIG. 6. The sandscreen assembly 1 can be installed in a production well system for producing fluids from multiple production zones as shown in FIG. 5.

Figure 7:
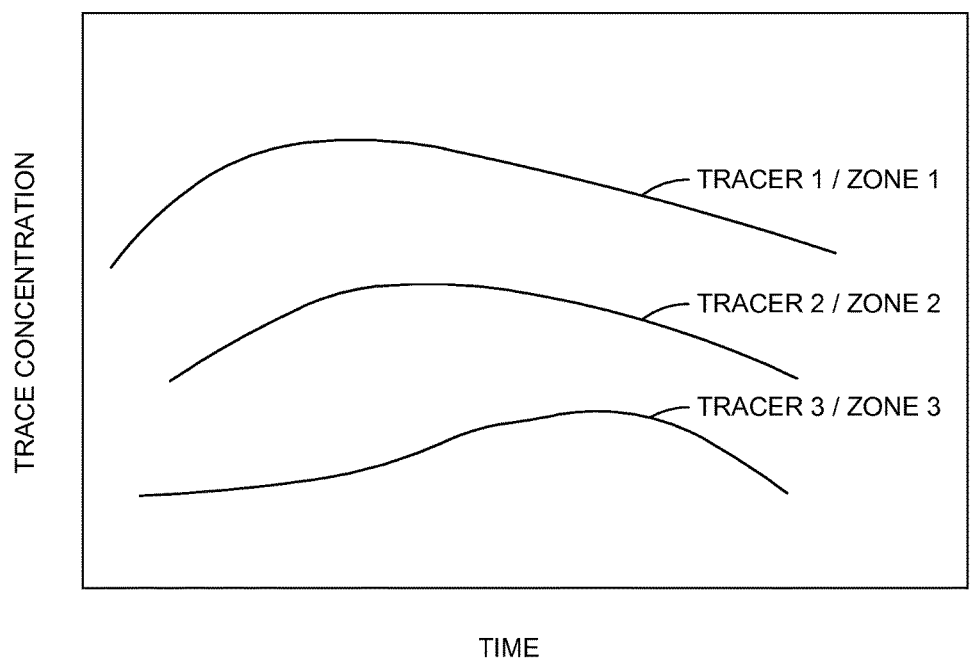
FIG. 7 illustrates the detection of different tracers from different zones.

In an embodiment, the tracer composites are used in a well having multiple production zones. The tracer composites used can be unique for each zones. For example, tracers in the trace composites disposed in each zone have different chemical structures. Based on the amount of measured tracers the amount of water flowing into the well at each zone can be calculated. As illustrated in FIG. 7, the concentrations of tracers 1, 2, and 3 indicate the water production levels at zones 1, 2, and 3. In another embodiment, the tracers for different zones are the same. When the water production information in a particular zone is needed, the tracer in the trace composite of that zone can be selectively activated thus providing information of water production in that zone.

Once a sample has been obtained, analysis for the presence and concentrations of the selected tracers may be carried out. Suitable instruments include, but are not limited to, gas chromatography (GC) using flame ionization detectors, electron capture detectors, and the like; liquid chromatography (LC), infrared (IR) spectroscopy; mass spectroscopy (MS); combination instrumentation such as Fourier transform infrared (FTIR) spectroscopy, GC-MS, LC-MS, and the like. The tracer may be detectable at a range of from about 1 ppt to about 1,000 ppm, about 5 ppt to about 1,000 ppm, or about 50 ppt to about 500 ppm. Once the tracer concentration has been determined, the information may be used in a variety of ways. For example, the concentration of detected tracers can provide information of the flow rate of produced water. Downhole water production detection and quantitative analysis method disclosed herein can be used for single zone or multiple zones for conventional oil and gas, deepwater, unconventional oil and gas, and stream-assisted gravity drainage applications.

All ranges disclosed herein are inclusive of the endpoints, and the endpoints are independently combinable with each other. "Or" means "and/or." "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like. "A combination thereof" means "a combination comprising one or more of the listed items and optionally a like item not listed." All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. Further, it should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity).

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A tracer composite comprising a tracer disposed in a metal-based carrier which comprises:
   a cellular nanomatrix having a thickness of about 10 nanometers to about 200 micros; and a metal matrix disposed in the cellular nanomatrix, the metal matrix comprising particles having a size of about 50 nanometers to about 800 microns and being surrounded by the cellular nanomatrix; and a tracer composite core which has a slower disintegrating rate than the metal-based carrier when measured at the same testing conditions, the tracer and the metal-based matrix being disposed on a surface of the tracer composite core, and the tracer composite sore comprising a material that is consolidated or forged from coated particles having a particle core comprising magnesium (Mg) metal or a magnesium (Mg) alloy, and a coating comprising one or more of the following: aluminum (Al), nickel (Ni), iron (Fe), tungsten (W), copper (Cu), or cobalt (Co);

wherein the tracer is detectable at a minimum concentration of from about 1 part per trillion (ppt) to about 1,000 parts per million (ppm) in a fluid produced from at least one zone of a well, the tracer comprises one or more of the following: an inorganic anion, an isotope, an activatable element, or an organic compound; and the metal-based carrier controllably releases the tracer in the presence of water in the fluid produced from at least one zone of the well.

2. The tracer composite of claim 1, wherein the tracer is present in an amount of 1 to 70 volume percent (vol. %) based on the total volume of the tracer composite.

3. The tracer composite of claim 1, wherein the tracer composite further comprises an outer member disposed on a surface of the tracer composite.

4. The tracer composite of claim 3, wherein the outer member has a plurality of apertures.

5. The tracer composite of claim 3, wherein the outer member has a slower disintegrating rate than the metal-based carrier when tested at the same testing conditions.

6. The tracer composite of claim 1, wherein the metal matrix comprises magnesium; and the cellular nanomatrix comprises one or more of the following: aluminum, calcium, cobalt, copper, iron, magnesium, molybdenum, nickel, silicon, zinc, or an intermetallic compound thereof, and the metal matrix is compositionally different from the cellular nanomatrix.

7. The tracer composite of claim 6, wherein the metal-based carrier further comprises a disintegration agent comprising one or more of the following: cobalt; copper; iron; or nickel.

8. The tracer composite of claim 1, wherein the inorganic anion comprises one or more of the following: $Au(CN)_2^-$; $Ni(CN)_4^{2-}$, $Co(CN)_6^{3-}$, $Fe(CN)_6^{3-}$, $NO_3^-$; $I^-$; or $SCN^-$.

9. The tracer composite of claim 1, wherein the isotope comprises one or more of the following: $^{16}O$; $^{18}O$; $^{14}N$; $^{15}N$; $^{32}S$; $^{34}S$; $^{36}S$; $^{12}C$; $^{13}C$; $^{86}Sr$; $^{87}Sr$; $^{1}H$; $^{2}H$; $^{10}B$; $^{11}B$; $^{35}Cl$, or $^{37}Cl$.

10. The tracer composite of claim 1, wherein the activatable element comprises one or more of the following: $^{69}Ga(n, 2n)^{68}Ga$, $^{121}Sb(n, 2n)^{120}Sb$, $^{138}Ba(n, 2n)^{137m}Ba$, or $^{63}Cu(n, 2n)^{62}Cu$.

11. The tracer composite of claim 1, wherein the tracer comprises one or more of the following: pentafluorobenzoate; meta-trifluoromethylbenzoate; tetrafluorophthalate; 2,3-difluorobenzoic acid; 2,3-dimethylbenzoic acid; 2,4,6-trimethylbenzoic acid; 2,4-dimethylbenzoic acid; 2,4-difluorophenylacetic acid; 2,4-dimethylbenzoic acid; 2,5-dimethylbenzoic acid; 2,5-dimethylbenzenesulfonic acid; 2,6-difluorobenzoic acid; 2,6-difluorophenylacetic acid; 2,6-dimethylbenzoic acid; 3,4-difluorobenzoic acid; 3,4-dimethylbenzoic acid; 3,5-dimethylbenzoic acid; 3,5-di(trifluoromethyl)benzoic acid; 3,5-di(trifluoromethyl)phenylacetic acid; 3-fluoro-4-methylbenzoic acid; 4-ethylbenzenesulfonic acid; 4-ethylbenzenesulfonic acid; 4-methylbenzenesulfonic acid; benzoic acid; benzenesulfonic acid; isophthalic acid; meta-fluorobenzoic acid; meta-fluorophenylacetic acid; meta-trifluoromethylbenzoic acid; meta-trifluoromethylphenylacetic acid; ortho-fluorobenzoic acid; ortho-trifluorophenylacetic acid; ortho-trifluoromethylbenzoic acid; ortho-trifluoromethylphenylacetic acid; phthalic acid; perfluorobenzoic acid; perfluorobenzenesulfonic acid; perfluorophenylacetic acid; para-fluorobenzoic acid; para-fluorophenylacetic acid; para-trifluoromethylbenzoic acid; para-trifluoromethylphenylacetic acid; terephthalic acid; 1,3,6,8-pyrene tetrasulfonate; 1,5-naphthalene disulfonate; 1,3,6-naphthalene trisulfonate; 2-naphthalene sulfonate; or 2,7-naphthalene disulfonate.

12. An article comprising the tracer composite of claim 1.

13. The composite of claim 1, wherein the tracer is dispersed in the metal matrix.

14. The composite of claim 1, wherein the tracer is dispersed in the cellular nanomatrix.

15. The composite of claim 1, wherein the cellular nanomatrix is continuous.

16. A method of analyzing water in a fluid produced from at least one zone of a well, the method comprising:

introducing a tracer composite into the well;

obtaining a sample of the fluid produced from at least one zone of the well; and analyzing the tracer in the sample;

wherein the tracer composite comprises a tracer disposed in a metal-based carrier which comprises: a cellular nanomatrix having a thickness of about 10 nanometers to about 200 microns and a metal matrix disposed in the cellular nanomatrix, the metal matrix comprising particles having a size of about 50 nanometers to about 800 microns and being surrounded by the cellular nanomatrix, a tracer composite core which has a slower disintegrating rate than the metal-based carrier when measured at the same testing conditions, the tracer and the metal-based matrix being disposed on a surface of the tracer composite core, and the tracer composite sore comprising a material that is consolidated or forged from coated particles having a particle core comprising magnesium (Mg) metal or a magnesium (Mg) alloy, and a coating comprising one or more of the following: aluminum (Al), nickel (Ni), iron (Fe), tungsten (W), copper (Cu), or cobalt (Co) wherein the tracer is detectable at a minimum concentration of from about 1 part per trillion (ppt) to about 1,000 parts per million (ppm) in the fluid produced from at least one zone of the well; and the tracer comprises one or more of the following: an inorganic anion, an isotope, an activatable element, or an organic compound.

17. The method of claim 16, wherein analyzing the tracer comprises determining the concentration of the tracer using one or more of the following: gas chromatography (GC); liquid chromatography (LC); infrared spectroscopy (IR); mass spectroscopy (MS); Fourier transform infrared spectroscopy (FT-IR); GC-MS; or LC-MS.

18. The method of claim 16, wherein the tracer composite is included in a downhole article.

19. The method of claim 16, wherein separate tracer composites are included in separate downhole articles located at different zones of the well.

20. The method of claim 16, wherein the method further comprises determining the flow rate of water in the produced fluid.

21. The method of claim 16, wherein the method further comprises selectively activate the tracer of the tracer composite disposed at a first zone of the well to analyze water in a fluid produced from the first zone.

* * * * *